United States Patent
Du

(10) Patent No.: US 10,231,976 B2
(45) Date of Patent: *Mar. 19, 2019

(54) METHODS FOR THE USE OF PROGESTOGEN AS A GLUCOCORTICOID SENSITIZER

(75) Inventor: Tao Tom Du, North Potomac, MD (US)

(73) Assignee: PRAIRIE PHARMACEUTICALS LLC, Bethesda, MD (US)

( * ) Notice: Subject to any disclaimer, the term of this patent is extended or adjusted under 35 U.S.C. 154(b) by 91 days.

This patent is subject to a terminal disclaimer.

(21) Appl. No.: 13/021,950

(22) Filed: Feb. 7, 2011

(65) Prior Publication Data

US 2011/0195031 A1    Aug. 11, 2011

Related U.S. Application Data

(60) Provisional application No. 61/302,325, filed on Feb. 8, 2010.

(51) Int. Cl.
*A61K 31/56*    (2006.01)
*A61K 31/57*    (2006.01)

(52) U.S. Cl.
CPC .............. *A61K 31/56* (2013.01); *A61K 31/57* (2013.01); *Y02A 50/402* (2018.01)

(58) Field of Classification Search
CPC .................................. A61K 31/56; A61K 31/57
See application file for complete search history.

(56) References Cited

U.S. PATENT DOCUMENTS

| | | | |
|---|---|---|---|
| 2001/0033870 A1* | 10/2001 | Luo .................. | A61K 9/0014 424/688 |
| 2002/0173669 A1 | 11/2002 | Schultz et al. | |
| 2004/0162274 A1* | 8/2004 | Paust et al. ................. | 514/177 |
| 2004/0234610 A1 | 11/2004 | Hall et al. | |
| 2005/0042268 A1* | 2/2005 | Aschkenasy ......... | A61K 9/0014 424/448 |
| 2006/0052306 A1 | 3/2006 | Costantino et al. | |
| 2006/0182691 A1 | 8/2006 | Besse et al. | |
| 2006/0275360 A1 | 12/2006 | Ahmed et al. | |
| 2007/0178166 A1 | 8/2007 | Bernstein et al. | |
| 2008/0269178 A1 | 10/2008 | Miller et al. | |
| 2009/0035375 A1 | 2/2009 | Skrtic et al. | |
| 2009/0221544 A1 | 9/2009 | Stein et al. | |
| 2010/0316724 A1* | 12/2010 | Whitfield ............. | A61K 9/0075 424/489 |
| 2011/0262502 A1 | 10/2011 | Lee et al. | |
| 2013/0203717 A1 | 8/2013 | Gil et al. | |
| 2016/0045517 A1 | 2/2016 | Du et al. | |

FOREIGN PATENT DOCUMENTS

WO    WO 2006138518 A1 *  12/2006
WO    WO-2011/097571 A2    8/2011

OTHER PUBLICATIONS

Ettmeyer, Lessons Learned from Marketed and Investigational Prodrugs, J. Medicinal Chem. 47: 2393-2404 (2004).*
Vippagupta et al., Advanced Drug Delivery Rev. 48: 3-26 (2001).*
Poulin et al. Breast Cancer Res Treatment 13: 161 (1989).*
Ringold et al., J Amer Chem Soc 78: 816-819 (1956).*
Guthrie et al. Endocrinology 107: 1393 (1980).*
van Rossum et al, Glucocorticoid Resistance, Endocr Dev. 2011;20:127-36.*
Beynon H L., "Severe premenstrual exacerbations of asthma: effect of intramuscular progesterone", Lancet 2(8607): 370-372 (Aug. 13, 1988).*
Saaresranta et al., Respiratory Res 6:28 (2005).*
Merck Index table of progestogens.*
Mantovani et al., "Medroxyprogesterone acetate reduces the in vitro production of cytokines and serotonin involved in anorexia/cachexia and emesis by peripheral blood mononuclear cells of cancer patients", Eur J Cancer 33: 602-607 (1997).*
Eugynon 30 review [downloaded from the website https://web.archive.org/web/20080421032737/http://www.ciao.co.uk/Eugynon_30_Review_5404407 on Aug. 1, 2016].*
Patient Group Direction for Microgynon 30 [downloaded from the website http://www.nes.scot.nhs.uk/media/422760/pgd_microgynon_30_dec_06.pdf on Aug. 1, 2016].*
Attardi et al., Amer J Obstetrics Gyn 197: 599.e.1 (2007).*
Ito et al., "Mode of Glucocorticoid Actions in Airway Disease", The Scientific World Journal 6: 1750-1769 (2006).*
Creed et al., "The effects of cytokines on suppression of lymphocyte proliferation by dexamethasone", J Immunol 183: 164-171 (2009) (Year: 2009).*
International Search Report dated Oct. 25, 2011, issued in corresponding International Application No. PCT/US2011/023917.
Office Action dated Jan. 17, 2017, by the U.S. Patent and Trademark Office in related U.S. Appl. No. 14/860,578 (30 pages).
Kam, J C., et. al. "Combination IL-2 and IL-4 reduces glucocorticoid receptor binding affinity and T cell response to glucocorticoids." J. Immunol. 1993. 151: 3460-3466.

(Continued)

*Primary Examiner* — Sue X Liu
*Assistant Examiner* — Thor Nielsen
(74) *Attorney, Agent, or Firm* — Foley & Lardner LLP

(57) ABSTRACT

Provided are methods and kits for administering progestogen as a glucocorticoid sensitizer to restore corticosteroid sensitivity or reverse the glucocorticoid insensitivity or enhance glucocorticoid sensitivity, in order to treat one or more glucocorticoid insensitivity related diseases or conditions. For example, these include methods for reversing the glucocorticoid insensitivity in a subject having no history of menstrual cycle-related exacerbation or allergy to self-hormones, particularly progesterone, such as premenstrual or perimenstrual deterioration in the symptoms, e.g., premenstrual worsening of atopic dermatitis or premenstrual exacerbations of asthma, and exhibiting relatively or totally refractory responses to glucocorticoid therapy, e.g., glucocorticoid resistance. The methods and kits provide for the administration of a sex hormone to the subject who is corticosteroid dependent or corticoid resistant or unresponsive or intolerant to corticosteroids.

16 Claims, 12 Drawing Sheets

(56) References Cited

OTHER PUBLICATIONS

Falchetti R., et al. "Determination of cytokine co-expression in individual splenic CD4+ and CD8+ T cells from influenza virus-immune mice." Immunology Nov. 1998;95(3):346-351, abstract.
Website Screenshot (http://www.nlm.nih.gov/medlineplus/immunesystemanddisorders.html), 2010.
MacIntyre N.R. "Chronic obstructive pulmonary disease (COPD) is a progressive disorder characterized in part by chronic inflammation of the airways of the lungs". Respir Care, 2010.
Nuñez B., et. al. "Antibodies Are Related to Lung Function in Obstructive Pulmonary Disease." Am J Respir Crit Care Med. Apr. 15, 2011;183(8):1025-31.
Yan R., et al. "Metabolism of 17α-hydroxyprogesterone caproate by hepatic and placental microsomes of human and baboons." Biochem. Pharmacol. 2008, 75(9):1848-1857.
Dalton K. "Progesterone or progestogens?" Br Med J 1976;2:1257.
Romero R., et. al., Progesterone is not the same as 17alpha-hydroxyprogesterone caproate: implications for obstetrical practice, Am. J. Obstet Gynecol. 2013, 208(6)421-426.
Office Action dated Jul. 25, 2017, by the U.S. Patent and Trademark Office in related U.S. Appl. No. 14/860,578 (22 pages).
Office Action dated Jul. 24, 2017, by the U.S. Patent and Trademark Office in related U.S. Appl. No. 14/860,680 (86 pages).
Tan et al. "IL-17 in Lung Disease: Friend or Foe?" Thorax 2013 68: pp. 788-790 (4 pages).
Beynon et. al. "Severe Premenstrual Exacerbations of Asthma: Effect of Intramuscular Progesterone" the Lancet 1988 (3 pages).
Ito et al. "Mode of Glucocorticoid Actions in Airway Disease" The Scientific World Journal, Sep. 7, 2006 pp. 1750-1769 (21 pages).
Allen, J. et al. (2015) "IL-17 and neutrophils: unexpected players in the type 2 immune response," Current Opinion in Immunology 34:99-106.
Amara, S. et al. (2015) "Synergistic effect of pro-inflammatory TNFalpha and IL-17 in periostin mediated collagen deposition: Potential role in liver fibrosis," Molecular Immunology 64(1):26-35.
Araya-Sibaja, A.M. et al. (2014) "Dissolution properties, solid state transformation and polymorphic crystallization: progesterone case study," Pharm Dev Technol. 19(7):779-788.
Aujla, S.J. et al. (2008) "IL-22 mediates mucosal host defense against Gram-negative bacterial pneumonia," Nature Medicine 14(3):275-281.
Barnes, P.J. (2010) "Mechanisms and resistance in glucocorticoid control of inflammation," J Steroid Biochem Mol Biol. 120(2-3):76-85.
Bauer, J.F. (2009) "Pharmaceutical Solids—The Amorphous State," Journal of Validation Technology 15(3):63-68.
Bhavsar, P. et al. (2008) "Relative corticosteroid insensitivity of alveolar macrophages in severe asthma compared with non-severe asthma," Thorax 63(9):784-789.
Boardman, C. et al. (2014) "Mechanisms of glucocorticoid action and insensitivity in airways disease," Pulmonary Pharmacology & Therapeutics 29(2):129-143.
Busse, W.W. et al. (2013) "Randomized, Double-Blind, Placebo-controlled Study of Brodalumab, a Human Anti-IL-17 Receptor Monoclonal Antibody, in Moderate to Severe Asthma," Am J Respir Crit Care Med. 188(11):1294-1302.
Caramori, G. et al. (2014) "Cytokine Inhibition in the Treatment of COPD," International Journal of COPD 9:397-412.
Caritis, S.N. et al. (2011) "Pharmacokinetics of 17-hydroxyprogesterone caproate in multifetal gestation," Am J Obstet Gynecol. 205(1):40.e1-40.e8.
Chew, N.Y.K. et al. (2002) "Effect of Powder Polydispersity on Aerosol Generation," J Pharm Pharmaceut Sci. 5(2):162-168.
Chikhalia, V. et al. (2006) "The effect of crystal morphology and mill type on milling induced crystal disorder," European Journal of Pharmaceutical Sciences 27(1):19-26.
Chrousos, G.P. (2014) "Hyperaldosteronism Differential Diagnoses," Hyperaldosteronism Differential Diagnoses. Medscape, Web.

Chung, K.F. et al. (2011) "p38 Mitogen-Activated Protein Kinase Pathways in Asthma and COPD," Chest 139(6):1470-1479.
Cornelius, D.C. et al. (2015) "A role for TH17 cells and IL-17 in mediating the pathophysiology associated with preeclampsia," Abstracts/Pregnancy Hypertension: An International Journal of Women's Cardiovascular Health 5:2-52.
Coulthard, L.R. et al. (2009) "p38MAPK: stress responses from molecular mechanisms to therapeutics," Trends Mol Med. 15(8):369-379.
De Pasquale, L. et al. (2012) "Increased muscle expression of interleukin-17 in Duchenne muscular dystrophy," Neurology 78:1309-1314.
Djupesland, P.G. (2013) "Nasal drug delivery devices: characteristics and performance in a clinical perspective—a review," Drug Deliv and Transl Res. 3(1):42-62.
Dvorsky, R. et al. (2011) "Dynamics analysis of cavitation disintegration of microparticles during nanopowder preparation in a new Water Jet Mill (WJM) device," Advanced Powder Technology 22:639-643.
Emamaullee, J.A. et al. (2009) "Inhibition of Th17 Cells Regulates Autoimmune Diabetes in NOD Mice," Diabetes Journals 58:1302-1311.
Final Office Action in U.S. Appl. No. 14/860,680, dated Feb. 8, 2018.
Francois, A. et al. (2014) "B cell activating factor is central to bleomycin- and IL-17-mediated experimental pulmonary fibrosis," Journal of Autoimmunity 56:1-11.
Fujino, S. et al. (2003) "Increased expression of interleukin 17 in inflammatory bowel disease," Gut 52:65-70.
Garfield, R.E. et al. (2012) "Use of progesterone and progestin analogs for inhibition of preterm birth and other uterine contractility disorders," FVV in ObGyn 4(4):237-244.
Gil, M. et al. (2010) "Scale-up methodology for pharmaceutical spray drying," Chemistry Today 28(4):18-22.
Gold, R. et al. (2008) "Interleukin-17-Extended Features of a Key Player in Multiple Sclerosis," The American Journal of Pathology 172(1):8-10.
Gong, F. et al. (2015) "The paradoxical role of IL-17 in atherosclerosis," Cellular Immunology 297(1):33-39.
He, D. et al. (2012) "IL-17 Mediated Inftammation Promotes Tumor Growth and Progression in the Skin," PLoS One. 7(2):e32126.
Honkanen, J. et al. (2010) "IL-17 Immunity in Human Type 1 Diabetes," J Immunol. 185:1959-1967.
Hueber, W. et al. (2010) "Effects of AIN457, a Fully Human Antibody to Interleukin-17A, on Psoriasis, Rheumatoid Arthritis, and Uveitis," Science Translational Medicine 2(52):52ra72.
Hueber, W. et al. (2012) "Secukinumab, a human anti-IL-17A monoclonal antibody, for moderate to severe Crohn's disease: unexpected results of a randomized, double-blind placebo-controlled trial," Gut; 61(12):1693-1700.
Irusen, E. et al. (2002) "p38 Mitogen-activated protein kinase-induced glucocorticoid receptor phosphorylation reduces its activity: Role in steroid-insensitive asthma," J Allergy Clin Immunol. 109:649-657.
Janssens, J.P. et al. (1999) "Physiological changes in respiratory function associated with ageing," Eur Respir J. 13:197-205.
Junghanns, J-U.A.H. et al. (2008) "Nanocrystal Technology, Drug Delivery and Clinical Applications," International Journal of Nanomedicine 3(3):295-310.
Junyaprasert, V.B. et al. (2015) "Nanocrystals for enhancement of oral bioavailability of poorly water soluble drugs," Asian Journal of Pharmaceutical Sciences 10(1):13-23.
Kang, M-J. et al. (2012) "IL-18 Induces Emphysema and Airway and Vascular Remodeling via IFN-g, IL-17A, and IL-13," Am J Respir Crit Care Med. 185(11):1205-1217.
Keck, C. et al. (2008) "Second generation of drug Nanocrystals for delivery of poorly soluble drugs: smart crystals technology," Dosis. 24(2):124-128.
Keck, C.M. et al. (2006) "Drug Nanocrystals of Poorly Soluble Drugs Produced by High Pressure Homogenization," European Journal of Pharmaceutics and Biopharmaceutics 62:3-16.
Keenan, C.R. et al. (2015) "Heterogeneity in mechanisms influencing glucocorticoid sensitivity: the need for a systems biology

(56) References Cited

OTHER PUBLICATIONS approach to treatment of glucocorticoid-resistant inflammation," Pharmacology & Therapeutics 150:81-93.
Khadka, P. et al. (2014) "Pharmaceutical particle technologies: an approach to improve drug solubility, dissolution and bioavailability," Asian Journal of Pharmaceutical Sciences 6:304-316.
Kim, Y-G. et al. (2012) "Gene Polymorphisms of Interleukin-17 and Interleukin-17 Receptor Are Associated with End-Stage Kidney Disease," Am J Nephrol. 36:472-477.
Kissi, Y.E. et al. (2014) "Increased Interleukin-17 and decreased BAFF serum levels in drug-free acute schizophrenia," Psychiatry Research 225 (1-2):58-63.
Knier, B. et al. (2015) "Neutralizing IL-17 protects the optic nerve from autoimmune pathology and prevents retinal nerve fiber layer atrophy during experimental autoimmune encephalomyelitis," Journal of Autoimmunity 56:34-44.
Konya C. et al. (2015) "Update on the role of Interleukin 17 in rheumatologic autoimmune diseases," Cytokine 75(2):207-215.
Krause, K.P. et al. (2000) "Heavy metal contamination of nanosuspension produced by high pressure homogenization," International Journal of Pharmaceutics 196(2):169-172.
Kudo, M. et al. (2012) "IL-17A produced by aB T cells drives airway hyper-responsiveness in mice and enhances mouse and human airway smooth muscle contraction," Nat Med. 18(4):547-554.
Kuon, R.J. et al. (2010) "Pharmacological actions of progestins to inhibit cervical ripening and prevent delivery depend upon their properties, the route of administration and the vehicle," Am J Obstet Gynecol. 202(5):455.e1-455.e9.
Labiris, N. R. et al. (2003) "Pulmonary drug delivery. Part I: Physiological factors affecting therapeutic effectiveness of aerosolized medications," British Journal Clinical Pharmacology 56(6):588-599.
Larran, J.M. (2005) "Micronisation of pharmaceutical powders for use in inhalation," Pharmaceutical Manufacturing and Packaging Sourcer. Spring 2005.
Leung, D.Y.M et al. (1997) "Association of Glucocorticoid Insensitivity with Increased Expression of Glucocorticoid Receptor B," J Exp Med. 186(9):1567-1574.
Lonare, A.A. et al. (2013) "Antisolvent crystallization of poorly water soluble drugs," International Journal of Chemical Engineering and Applications 4(5):337-341.
Mantovani, A. et al. (2008) "Cancer related inflammation," Nature 454(7203):436-444.
Martinu, T. et al. (2015) "IL-17 Mediates Post-Transplant Airways and Parenchymal Lung Fibrosis," The Journal of Heart and Lung Transplantation, 34(4S):S175-S176, Abstract 463.
Masterisizer 2000 User Manual. MAN0384 Issue 1.0 Mar. 2007. Malvern Instruments Lid.
Milner, J.D. et al. (2008) "Impaired TH17 cell differentiation in subjects with autosomal dominant hyper-IgE syndrome," Nature 452(7188):773-776.
Mittelstadt, P.R. et al. (2009) "T Cell Receptor-mediated Activation of p38alpha by Mono-phosphorylation of the Activation Loop Results in Altered Substrate Specificity," J Biol Chem. 284(23):15469-15474.
Morishima, Y. et al. (2013) "Th17-Associated Cytokines as a Therapeutic Target for Steroid-Insensitive Asthma," Clinical and Developmental Immunology 2013:609395, 9 pages.
Moschwitzer, J.P. (2013) "Drug Nanocrystals in the commercial pharmaceutical development process," International Journal or Pharmaceutics 453:142-156.
Nakach, M. et al. (2004) "Comparison of various milling technologies for grinding pharmaceuticals," International Journal of Mineral Processing 74:S173-S181.
Nekkanti, V. et al. (2012) "Drug Nanoparticles—An Overview," The Delivery of Nanoparticles:111-132.
Newcomb, D.C. et al. (2015) "Ovarian Hormones Increase IL-17A Production from Th17 Cells through an IL-23B and Let-7f Mediated Pathway in Severe Asthma," J Allergy Clin Immunol. pii:S0091-6749(15)00840-4: AB230, Abstract 745.
Nold, C. et al. (2013) "Prevention of preterm birth by progestational agents: what are the molecular mechanisms?" Am J Obstet Gynecol. 208(3):223.e1-223.e7.
Novartis (2014) Web (https://www.novartis.com/news/media-releases/novartis-announces-fda-approval-first-il-17a-antagonist-cosentyxtm-secukinumab).
Ortiz, M.L. et al. (2015) "Immature myeloid cells directly contribute to skin tumor development by recruiting IL-17-producing CD4 T cells," J Exp Med. 212(3):351-367.
Oshiro, K. et al. (2011) "Interleukin-17A is involved in enhancement of tumor progression in murine intestine," Immunobiology 217(1):54-60.
Park, H. et al. (2005) "A distinct lineage of CD4 T cells regulates tissue inflammation byproducing interleukin 17," Nat Immunol. 6(11):1133-1141.
Patel, Y. et al. (2012) "Hydroxyprogesterone Caproate Injection (Makena) One Year Later, To Compound or Not to Compound—That is the Question," P&T 37(7):405-411.
Pinart, M. et al. (2013) "IL-17A Modulates Oxidant Stress-Induced Airway Hyperresponsiveness but Not Emphysema," Plos One 8(3):e58452, 1-8.
Potvin, S. et al. (2008) "Inflammatory Cytokine Alterations in Schizophrenia: A Systematic Quantitative Review," Society of Biological Psychiatry 63:801-808.
Qiao, G. et al. (2015) "A77 1726, the active metabolite of leflunomide, attenuates lupus nephritis by promoting the development of regulatory T cells and inhibiting IL-17-producing double negative T cells," Clinical Immunology 157(2):166-174.
Rathore, A.M. et al. (2015) Hormones in Obstetrics and Gynaecology, Jaypee Brothers Publishers.
Roussel, L. et al. (2010) "IL-17 Promotes p38 Mapk-Dependent Endothelial Activation Enhancing Neutrophil Recruitment to Sites of Inflammation," J Immunol. 184:4531-4537.
Roy, T. et al. (2012) "Epidemiology of depression and diabetes: a systematic review," Journal of Affective Disorders 142S1:S8-S21.
Ruddock, N. K. et al. (2008) "Progesterone, but not 17-alpha-hydroxyprogesterone caproate, inhibits human myometrial contractions," Am J Obstet Gynecol. 199:391.e1-391.e7.
Saijo, S. et al. (2010) "Dectin-2 Recognition of a-Mannans and Induction of Th17 Cell Differentiation Is Essential for Host Defense against Candida albicans," Immunity 32(5):681-691.
Sani, S.N. et al. (2009) "Effect of microfluidization parameters on the physical properties of PEG-PLGA nanoparticles prepared using high pressure microfLuidization," Journal of Microencapsulation 26(6):556-561.
Schindler, A.E. et al. (2003) "Classification and pharmacology of progestins," Maturitas 46(S1):S7-S16.
Scott-Moncrieff, J.C. et al. (1990) "Serum disposition of exogenous progesterone after intramuscular administration in bitches," Am J Vet Res. 51(6):893-895.
Seow, C.H. et al. (2015) "Downregulation of IL-17 Related Cytokines in the Second Trimester of Pregnancy Women With IBD Supports Pregnancy Driven Immunomodulatory Effects Involving the Th17 Pathway," Gas. 148(4):5454-5455, Abstract Su1262.
Sharma, P.H. et al. (2015) "Poorly Soluble Drugs—A Challenge in Drug Delivery System," European Journal of Pharmaceutical and Medical Research 2(2):484-502.
Shegokar, R. et al. (2010) "Nanocrystals: Industrially feasible multifunctional formulation technology for poorly soluble actives," International Journal of Pharmaceutics 399(1-2):129-139.
Stew, A. (2014) "Pulmonary Drug delivery—Particle Engineering for Inhaled Therapeutics," Pharmaceutical Technology 38(2).
Srivalli, K.M.R. et al. (2014) "Drug Nanocrystals: a way toward scale-up," Saudi Pharmaceutical Journal.
Stirling, R.G. et al. (2001) "Severe asthma: definition and mechanisms," Allergy 56:825-840.
Suzuki, H. et al. (2013) "Role of Complement Activation in Obliterative Bronchiolitis Post-Lung Transplantation," J Immunol. 191:4431-4439.

(56) References Cited

OTHER PUBLICATIONS

Tsoukas, A. et al. (2015) "Targeting the IL-17/IL-23 Axis in Chronic Inflammatory Immune-Mediated Diseases," Molecular Biology of B Cells (2nd Edition):527-539.
U.S. Food and Drug Administration (2015) "FDA approves new psoriasis drug Cosentyx," Web.
Vasanthakumar, R. et al. (2014) "Serum IL-9, IL-17, and TGF-beta levels in subjects with diabetic kidney disease (Cures-134)," Cytokine 72(1):109-112.
Vazquez-Tello, A. et al. (2013) "Glucocorticoid Receptor-Beta Up-Regulation and Steroid Resistance Induction by IL-17 and IL-23 Cytokine Stimulation in Peripheral Mononuclear Cells," J Clin Immunol. 33:466-478.
Vehring, R. (2008) "Pharmaceutical Particle Engineering via Spray Drying," Pharmaceutical Research 25(5):999-1022.
Vlahos, R. et al. (2014) "Recent advances in pre-clinical mouse models of COPD," Clinical Science (Lond) 126: 253-265.
Vroman, H. et al. (2015) "Mode of Dendritic Cell Activation: The Decisive Hand in Th2/Th17 Cell Differentiation. Implications in Asthma Severity?" Immunobiology 220(2):254-261.
Wei, J. et al. (2013) "IL-17 cytokines in immunity and inflammation," Emerging Microbes and Infections 2:e60.
Wu, D. et al. (2013) "Interleukin-17: A Promoter in Colorectal Cancer Progression," Clinical and Developmental Immunology 2013:436307.
Yang, N. et al. (2012) "Current Concepts in Glucocorticoid Resistance," Steroids 77:1041-1049.
Zijlstra, G.J. et al. (2012) "Interleukin-17A induces glucocorticoid insensitivity in human bronchial epithelial cells," Eur Respir 39:439-445.
Non-Final Office Action in U.S. Appl. No. 14/860,578, dated Apr. 6, 2018.
Non-Final Office Action in U.S. Appl. No. 14/860,680, dated Aug. 7, 2018.
Final Office Action in U.S. Appl. No. 14/860,578, dated Oct. 17, 2018.

* cited by examiner

METHODS FOR THE USE OF PROGESTOGEN AS A GLUCOCORTICOID SENSITIZER

CROSS-REFERENCE TO RELATED APPLICATIONS

This application claims priority to U.S. Provisional Patent Application Ser. No. 61/302,325 that was filed on Feb. 8, 2010, the entire disclosure of which is hereby incorporated by reference.

FIELD OF THE INVENTION

Glucocorticoid insensitivity presents a profound management problem in diseases/conditions treated with glucocorticoids because the therapy is not effective. The present invention relates to methods and kits for administering progestogen as a glucocorticoid sensitizer to restore corticosteroid sensitivity or reverse the glucocorticoid insensitivity or enhance glucocorticoid sensitivity, in order to treat one or more glucocorticoid insensitivity related diseases or conditions. For example, the present invention relates to methods for reversing the glucocorticoid insensitivity in a subject having no history of menstrual cycle-related exacerbation or allergy to self-hormones, particularly progesterone, such as premenstrual or perimenstrual deterioration in the symptoms, e.g., premenstrual worsening of atopic dermatitis or premenstrual exacerbations of asthma, and exhibiting relatively or totally refractory responses to glucocorticoid therapy, e.g., glucocorticoid resistance. The methods and kits of the present invention provide for the administration of a sex hormone to the subject who is corticosteroid dependent or corticoid resistant or unresponsive or intolerant to corticosteroids.

BACKGROUND OF THE INVENTION

Glucocorticoids are the first-line treatment for various immune-inflammatory and allergic diseases. For example, the autoimmune diseases include more than 70 chronic disorders that affect about 5% of the US population, and include those that most occur in women (>80%) such as Sjogren's syndrome, SLE, autoimmune thyroid disease (Hashimoto's thyroiditis and well as Graves' disease) and scleroderma, or relatively common among women (60-75%) such as rheumatoid arthritis (RA), multiple sclerosis (MS) and myasthenia gravis; or those that occur at a similar female:male ratio such as sarcoid and inflammatory bowel diseases. Glucocorticoid insensitivity presents a profound management problem in those diseases/conditions treated with steroids, and twenty to forty percent of patients may fail to achieve disease control. The glucocorticoid insensitivity may present as relatively or totally refractory to glucocorticoid therapy; unresponsive or intolerant to corticosteroids; unresponsive to an adequate induction dose of corticosteroids; initially responsive to corticosteroids but relapses quickly upon drug withdrawal or dose tapering (corticosteroid dependent); corticoid resistant, e.g., requires a very high dose treatment; or "difficult to treat" or severe condition. For example, 20-30% of patients with severe and steroid-resistant Crohn's Disease will not respond to steroid therapy (Michetti P, Mottet C, Juillerat P, Felley C, Vader J-P, Burnand B, Gonvers J-J, Froehlich F: Severe and Steroid-Resistant Crohn's Disease. Digestion 2005; 71:19-25).

Diseases/conditions related to glucocorticoid insensitivity may include: refractory inflammatory bowel disease, such as Refractory ulcerative colitis and children with severe Crohn disease, corticosteroid refractory asthma or glucocorticoid resistant asthma or symptomatic corticosteroid dependent asthma, desquamative interstitial pneumonia refractory to corticosteroid, refractory inflammatory myopathies, refractory myasthenia gravis, refractory pemphigus vulgaris, methotrexaterefractory RA patients, refractory nephrotic syndrome in adults, corticosteroid dependent systemic lupus erythematosus (SLE), primary Sjogren's syndrome, systemic vasculitis and polymyositis, chronic graft-versus-host disease, corticosteroid dependent or refractory multiple sclerosis, refractory sprue-like disease, steroid-resistant sarcoidosis, refractory mucosal lesions of pemphigus vulgaris, refractory Schnitzler syndrome, resistant dermatitis of the head and neck, severe refractory atopic dermatitis, refractory Idiopathic thrombocytopenia purpura, refractory orbital myositis, refractory or recurrent lymphomas, critically ill patients with sepsis or acute respiratory distress syndrome (ARDS) or relative adrenal insufficiency, corticosteroid-dependent conditions (e.g., rosacea, polymyalgia rheumatic, giant cell arteritis, polymyositis, dermatomyositis, Kawasaki syndrome, Guillain-Barre syndrome, chronic inflammatory demyelinating polyneuropathy, multifocal motor neuropathy, Stiff man syndrome etc.,). Glucocorticoid insensitivity has serious health, societal, and economic costs. For example, a small percentage of patients with asthma (5-10%) have severe corticosteroid-refractory condition that often fails to respond but these patients account for >50% of the total asthma health care costs.

Glucocorticoids suppress inflammation mainly as a result of both activation of anti-inflammatory genes and suppression of pro-inflammatory genes. The activation of anti-inflammatory gene expression starts as glucocorticoid binds cytosolic glucocorticoid receptor (GR), which is activated and translocates to the nucleus. Once in the nucleus, it binds to glucocorticoid response elements (GREs) and transcriptional coactivator molecules, and causes acetylation of core histones, which leads to the expression of anti-inflammatory genes. Inflammatory stimuli switch on multiple inflammatory genes that encode cytokines, chemokines, adhesion molecules, inflammatory enzymes, and receptors via pro-inflammatory transcription factors, such as nuclear factor κB (NFκB) and activator protein 1, and the recruitment of co-repressor molecules. Activated glucocorticoid receptors bind to the coactivators in the nucleus to inhibit histone acetyltransferase (HAT) activity directly and recruit histone deacetylase 2 (HDAC2), leading to suppression of the activated inflammatory genes.

Several possible molecular mechanisms of glucocorticoid resistance have been recognized, and include genetic susceptibility, lack of or defective binding to GR and translocation, reduced GR expression, lack of co-repressor activity, or enhanced activation of inflammatory pathways. For example, glucocorticoid receptors might be phosphorylated by several kinases (e.g., p38 mitogen-activated protein kinase, c-Jun N-terminal kinase, and extracellular signal-regulated kinase) that results in the defective binding, alterations in their stability, translocation to the nucleus, binding to DNA, and interaction with other proteins. Excessive activation of the transcription factor activator protein 1 can prevent GRs binding to glucocorticoid response elements (GREs) or inhibiting nuclear factor κB; Nitric oxide (NO) can nitrate tyrosine residues on GRs; GRs can also be ubiquitinated (Ub), which results in degradation of GR by the proteasome; reduced histone deacetylase-2 (HDAC2) expression, raised macrophage migration inhibitory factor, and increased P-glycoprotein-mediated drug efflux (Peter J Barnes, Ian M Adcock. Glucocorticoid resistance in inflammatory diseases. Lancet 2009; 373: 1905-17).

The clinical and biological mechanisms of steroid-dependency are not well understood compared with those determining steroid-resistance. Steroid-dependency and steroid-resistance may share some common intrinsic mechanisms while other mechanisms are simply clinical or pharmacological.

Many attempts have been made to ameliorate the effects of glucocorticoid insensitivity. A common approach is to use broad-spectrum anti-inflammatory treatments such as immunosuppressive or immunomodulators agents (e.g., cyclosporine, methotrexate, gold, 6-mercaptopurine, biologic products such as intravenous immunoglobulin and Mepolizumab), and calcineurin inhibitors (e.g., cyclosporin, tacrolimus). Various approaches have been proposed or developed to reverse glucocorticoid resistance such as p38 MAP kinase inhibitors, JNK inhibitors (decrease API), Vitamin D in steroid-resistant asthma (increase regulatory T cells), MIF inhibitors, Histone deacetylate-2 activators, Theophylline, Phosphoinositide-3-kinase-δ inhibitors, antioxidants, iNOS inhibitors and P-glycoprotein inhibitors. The use of progestogen for reversing the glucocorticoid-insensitivity has not been discussed or presented anywhere, and the present invention represents a significant, surprising and unexpected advance in the art.

The different approaches for management of glucocorticoid insensitivity have had limited success. Some agents may work in a condition, but not others. Methotrexate is effective for rheumatoid arthritis, but it might be ineffective in cases of glucocorticoid-resistant inflammatory bowel disease caused by increased P-glycoprotein expression. Similarly, calcineurin inhibitors are useful in some patients with glucocorticoid-resistant inflammatory bowel disease, but they have not proven to be effective in glucocorticoid-resistant asthma. Further, the uses of those agents are often associated with significant adverse events. A high percentage of patients (60-70%) may fail treatment with methotrexate because of side effects. Phosphodiesterase-4 inhibitors for COPD and inflammatory conditions have dose-limiting side-effects of nausea, diarrhea, and headaches. Significant toxicity and side-effects have hampered the drug development programs for p38 MAP-kinase inhibitors and selective inhibitors to block inhibition of NFκB kinase (IKKβ)/NFκB (Peter J Barnes, Ian M Adcock. Glucocorticoid resistance in inflammatory diseases. Lancet 2009; 373: 1905-17).

Given that a considerable proportion of patients with autoimmune, allergic, and lymphoproliferative diseases are refractory to glucocorticoid therapy as well many different inflammatory diseases share similar molecular mechanisms in glucocorticoid insensitivity, there exists a heretofore unmet need in the art for methods for developing a common therapeutic strategy to reverse the steroid-insensitivity. The use of progestogen, in accordance with the present invention, has been discovered to present a surprising, unexpected, and also practicable method to help patients with diseases/conditions that are unresponsive or intolerant to corticosteroids or corticosteroid dependent and resistant.

Progestogen products have been extensively used in a wide range of reproductive diseases/conditions for more than 60 years, and known to have anti-inflammatory effects. The majority of studies related to inflammatory responses were conducted in pregnancy-associated models. Progesterone/PR Maintains Uterine Quiescence via Antiinflammatory Actions (Carole R. Mendelson. Minireview: Fetal-Maternal Hormonal Signaling in Pregnancy and Labor Molecular Endocrinology 23: 947-954, 2009). Gellersen (2009) provided a comprehensive review of non-genomic progesterone actions, and summarized possible mechanisms of progesterone anti-inflammatory effects, including that progesterone opposes prostaglandin production in the uterus of pregnancy, partially by inhibiting cyclooxygenase (COX-2) expression; immunoregulatory function in human T-lymphocytes via G-protein activation and K+ channel Inhibition; progesterone-induced blocking factor (PIBF) acts on the phospholipase A2 enzyme, interferes with arachidonic acid metabolism, induces a Th2 biased immune response, and exerts an anti-abortive effect by controlling NK activity (Gellersen B et al. Non-genomic progesterone actions in female reproduction Human Reproduction Update, Vol. 15, No. 1 pp. 119-138, 2009). Another review by Challies (2009) suggests other possible mechanisms: progesterone blocks mitogen-stimulated lymphocyte proliferation, modulates antibody production, decreases the oxidative burst of monocytes, reduces the production of proinflammatory cytokines by macrophages in response to bacterial products, and alters cytokine secretion of T-cell clones to favor IL-10 production, upregulates Toll-like receptor 4 (TLR-4) expression and suppresses TLR-2 response to infection in intrauterine tissues, resulting in a protective role with respect to preterm delivery, inhibits basal and cytokine-enhanced matrix metalloproteinases (MMP)-1 and MMP-3 expression in cultured decidual cells demonstrating protection against preterm delivery (Challis J R et al. Inflammation and Pregnancy Reproductive Sciences 2009; 16; 206). Since the concept of using progestogen for reversing the glucocorticoid-insensitivity has not been disclosed, taught, suggested, discussed, or presented anywhere, the present discovery represents a significant and unexpected advance in the art.

Menstrual cycle-related exacerbation of common medical conditions is a well-recognized phenomenon, and may include migraine, epilepsy, asthma, irritable bowel syndrome, autoimmune progesterone dermatitis and stomatitis, and diabetes. Exacerbation is influenced by hormonal changes of the menstrual cycle. The majority of these effects occur during the luteal and menstrual phases of the cycle. For example, premenstrual asthma denotes worsening of asthma symptoms shortly before and/or during menstruation. Accurate documentation of symptoms on a menstrual calendar allows identification of women with cyclic alterations in disease activity. Female sex-steroid hormones play an important role but the exact mechanism is still unknown. Several theories exist to explain these menstrual cycle-related effects. These include fluctuations in levels of sex steroids, cyclic alterations in the immune system, increased airway hyperresponsiveness, changing perceptions of disease severity brought about by premenstrual alterations in mood, as seen in premenstrual syndrome, and allergy to self-hormones particularly progesterone. Menstrual cycle-related exacerbation might be ameliorated by progesterone supplementation [Allison M. Case and Robert L. Reid. Menstrual cycle effects on common medical conditions. Journal Comprehensive Therapy Issue Volume 27, Number 1/March, 2001; Beynon H L. Severe premenstrual exacerbations of asthma: effect of intramuscular progesterone. Lancet—13-Aug.-1988; 2(8607): 370-2; Roby, Russell R et al. Sublingual progesterone dilutions as bronchodilator in asthmatic females. World Allergy Organization Journal: November 2007—Volume—Issue—p S148].

Glucocorticoid insensitivity often correlates with other factors believed to contribute to relatively or totally refractory responses to glucocorticoid therapy. These include the various risk factors noted above such as genetic susceptibility, abnormalities in the glucocorticoid receptor gene, viral infection and oxidative stress. For example, oxidative DNA damage is known to be a primary cause of the process of mutation and a leading cause of aging, cancer and other diseases because guanine, one of the four basic nucleotides that make up DNA and form the genetic code of life, is particularly sensitive to oxidative damage, and a predominant number of genetic mutations are linked to guanine. Thus, there exists a need in the art for methods for reducing the occurrence of glucocorticoid insensitivity related conditions (e.g., refractory asthma, refractory rheumatoid arthritis, refractory inflammatory bowel disease, chronic obstructive pulmonary disease and acute respiratory distress syndrome) associated with such risk factors.

A menstrual rhythm has been documented for exacerbations of asthma, which may have important clinical relevance to the patient with severe asthma. Beynon et al. (1988) reported 3 cases of severe premenstrual exacerbations of asthma that were treated with intramuscular progesterone. The patients hadn't responded to conventional treatment, including high-dose corticosteroids. In all cases there was a fall premenstrually in peak flow rate. The addition of intramuscular progesterone (100 mg daily in two cases and 600 mg twice a week in one) to the regimen eliminated the premenstrual dips in peak flow, and daily doses of prednisolone were reduced in the three patients. The above-described study and results are described in Beynon et al. (Severe premenstrual exacerbations of asthma: effect of intramuscular progesterone. Lancet—13-Aug.-1988; 2(8607): 370-2.).

In another study, Russell R et al (2007) tested the hypothesis that pre-menstrual asthma is associated with allergy to self-hormones particularly progesterone by using sublingual progesterone dilutions as bronchodilator. Sixteen females who had a previous diagnosis of severe asthma and who were nebulization dependent were selected for the study. Spirometric studies were performed on these subjects. Study showed changes over time of the forced expiratory volume in one second (FEV1), the forced vital capacity (FVC), and the peak expiratory flow (PEF) measured at three times: (1) before treatment, (2) after sublingual normal saline treatment (3) after sublingual progesterone treatment. After treatment with sublingual progesterone, twelve of the sixteen patients (75%) experienced a bronchodilator effect (greater than 12% increase) in either FEV1 or FVC. Eight (50%) experienced an increase in both FEV1 and FVC. Eight (50%) had an increase of 27% or greater in PEF. The above-described study and results are described in Russell R et al. (Sublingual progesterone dilutions as bronchodilator in asthmatic females. World Allergy Organization Journal: November 2007—Volume—Issue—p S148.).

Activation of mitogen-activated protein kinases (MAPKs) is a critical event in mitogenic signal transduction. Ruzycky A L (1996) determined the effects of 17 beta-estradiol and progesterone on mitogen-activated protein kinase expression and activity. MAPK expression and activity was examined in uterine smooth muscle from rats pretreated with estradiol-17 beta alone or with estradiol-17 beta and progesterone. MAPK expression was detected by immunoblotting using erk1/2 antibodies. MAPK activity was detected by measurement of the phosphorylation of a MAPK-specific peptide sequence of myelin basic protein. Steroid treatment caused a modest (20%) decline in erk 1 and 2 expression in membrane and cytosolic fractions. Both estrogen and progesterone increased MAPK tyrosine phosphorylation and membrane-associated MAPK activity. Steroid treatment increased cytosolic MAPK tyrosine phosphorylation, but not enzymatic activity. The above-described study and results are described in Ruzycky A L (Effects of 17 beta-estradiol and progesterone on mitogen-activated protein kinase expression and activity in rat uterine smooth muscle. Eur J Pharmacol. 1996 Apr. 11; 300(3):247-54).

SUMMARY OF THE INVENTION

Certain embodiments of the present invention are directed to methods for restoring corticosteroid sensitivity or reversing the glucocorticoid insensitivity or enhancing glucocorticoid sensitivity.

Other embodiments of the present invention are directed to methods for administering a pharmaceutical composition comprising a steroid hormone to a subject having no history of menstrual cycle-related exacerbation, and suffering from one or more glucocorticoid insensitivity related conditions. Glucocorticoid insensitivity related conditions include, for instance, a range of corticoid resistant diseases and immune-inflammatory disorders treated with steroids when the therapy becomes ineffective or intolerant or dependent or unresponsive or refractory to corticosteroids, and combinations thereof.

In one embodiment, a method of the present invention comprises administering a pharmaceutical composition comprising a steroid hormone to a subject having no history of menstrual cycle-related exacerbation, wherein the subject is at risk for developing glucocorticoid insensitivity due to exposure to oxidative stress.

Yet other embodiments of the present invention are directed to methods for restoring corticosteroid sensitivity or reversing the glucocorticoid insensitivity or enhancing glucocorticoid sensitivity, and treating one or more conditions selected from the group consisting of corticoid resistant diseases, corticosteroid refractory, corticosteroid-dependent immune-inflammatory disorders, and combinations thereof. Certain exemplary glucocorticoid resistant conditions include, but are not limited to, glucocorticoid resistant asthma, refractory rheumatoid arthritis, refractory inflammatory bowel disease, chronic obstructive pulmonary disease and acute respiratory distress syndrome, interstitial pulmonary fibrosis, and cystic fibrosis. Certain exemplary glucocorticoid refractory conditions include, but are not limited to, refractory ulcerative colitis, children with severe Crohn disease, corticosteroid refractory asthma, desquamative interstitial pneumonia refractory to corticosteroid, refractory inflammatory myopathies, refractory myasthenia gravis, refractory pemphigus vulgaris, methotrexate-refractory RA patients, refractory nephrotic syndrome, refractory multiple sclerosis, refractory sprue-like disease, steroid-resistant sarcoidosis, refractory mucosal lesions of pemphigus vulgaris, refractory Schnitzler syndrome, resistant dermatitis of the head and neck, severe refractory atopic dermatitis, refractory Idiopathic thrombocytopenia purpura, refractory orbital myositis, refractory or recurrent lymphomas, critically ill patients with sepsis or acute respiratory distress syndrome (ARDS) and relative adrenal insufficiency. Certain exemplary glucocorticoid dependent conditions include, but are not limited to, rosacea, polymyalgia rheumatic, giant cell arteritis, polymyositis, dermatomyositis, Kawasaki syndrome, Guillain-Barre syndrome, chronic inflammatory demyelinating polyneuropathy, multifocal motor neuropathy, Stiff man syndrome, corticosteroid dependent systemic lupus erythematosus, corticosteroid dependent multiple sclerosis, symptomatic corticosteroid dependent asthma, primary Sjogren's syndrome, systemic vasculitis and polymyositis, organ transplants, graft-versus-host disease, and glucocorticoid dependent cancer.

Still other embodiments of the present invention are directed to kits comprising (i) a pharmaceutical composition comprising a steroid hormone and one or more pharmaceutically acceptable excipients; and (ii) instructions for administering the pharmaceutical composition to a subject preferably having no history of menstrual cycle-related exacerbation, and suffering from one or more glucocorticoid insensitivity related conditions. Glucocorticoid insensitivity related conditions include, for instance, a range of corticoid resistant diseases and immune-inflammatory disorders treated with steroids when the therapy becomes ineffective or intolerant or dependent or unresponsive or refractory to corticosteroids, and combinations thereof.

In another embodiment, the kits of the present invention comprise (i) a pharmaceutical composition comprising a steroid hormone and one or more pharmaceutically acceptable excipients; and (ii) instructions for administering the pharmaceutical composition to a subject who is at high risk to develop glucocorticoid insensitivity, but preferably has no history of menstrual cycle-related exacerbation, and preferably is at risk for developing one or more glucocorticoid insensitivity related conditions due to oxidative stress.

Yet other embodiments of the present invention are directed to kits comprising (i) a pharmaceutical composition comprising a steroid hormone and one or more pharmaceutically acceptable excipients; and (ii) instructions for administering the pharmaceutical composition to a subject that preferably has no history of menstrual cycle-related exacerbation, and wherein the subject is suffering from one or more glucocorticoid insensitivity related conditions in order to achieve the glucocorticoid-sensitizer effects of steroid-sparing in corticosteroid-dependent patients, better responsiveness or tolerance to corticosteroids, achieving efficacy by using a lower dose of corticosteroid, preventing individuals at risk for developing corticosteroid refractory responses or resistance or exacerbations in response to antigen exposures, infections, exercise, or irritants, achieving optimal immune-functions, easier responses for the subject or patient when steroid administration is tapered or withdrawn, or in prolonged administration of corticosteroids, decreased risks for developing corticosteroid-related adverse events such as opportunistic infections and bone loss, and combinations thereof.

It is to be understood that the embodiments described above are provided as representative embodiments of the present invention, and in no way are to be construed as limiting the scope of the present invention.

BRIEF DESCRIPTION OF THE DRAWINGS

FIG. 1 depicts IL-2 levels at baseline, after PHA stimulation and dose-dependent inhibition of IL-2 by dexamethasone.

FIG. 2 depicts that addition of IL-2 and IL-4 induces steroid resistance.

FIG. 3 depicts progestogen's effects (% Imax) in reversing steroid resistance: comparing 17HPC, P4 and MPA under low dose Dexamethasone (hereinafter, "Dexamethasone") ($10^{-10}$ M).

FIG. 4 depicts progestogen's effects (% Imax) in reversing steroid resistance: comparing 17HPC, P4 and MPA under high dose Dexamethasone ($10^{-6}$ M).

FIG. 5 depicts that 17HPC restores corticosteroid sensitivity.

FIG. 6 depicts that 17HPC reverses steroid resistance and individual response patterns.

Figure 6:
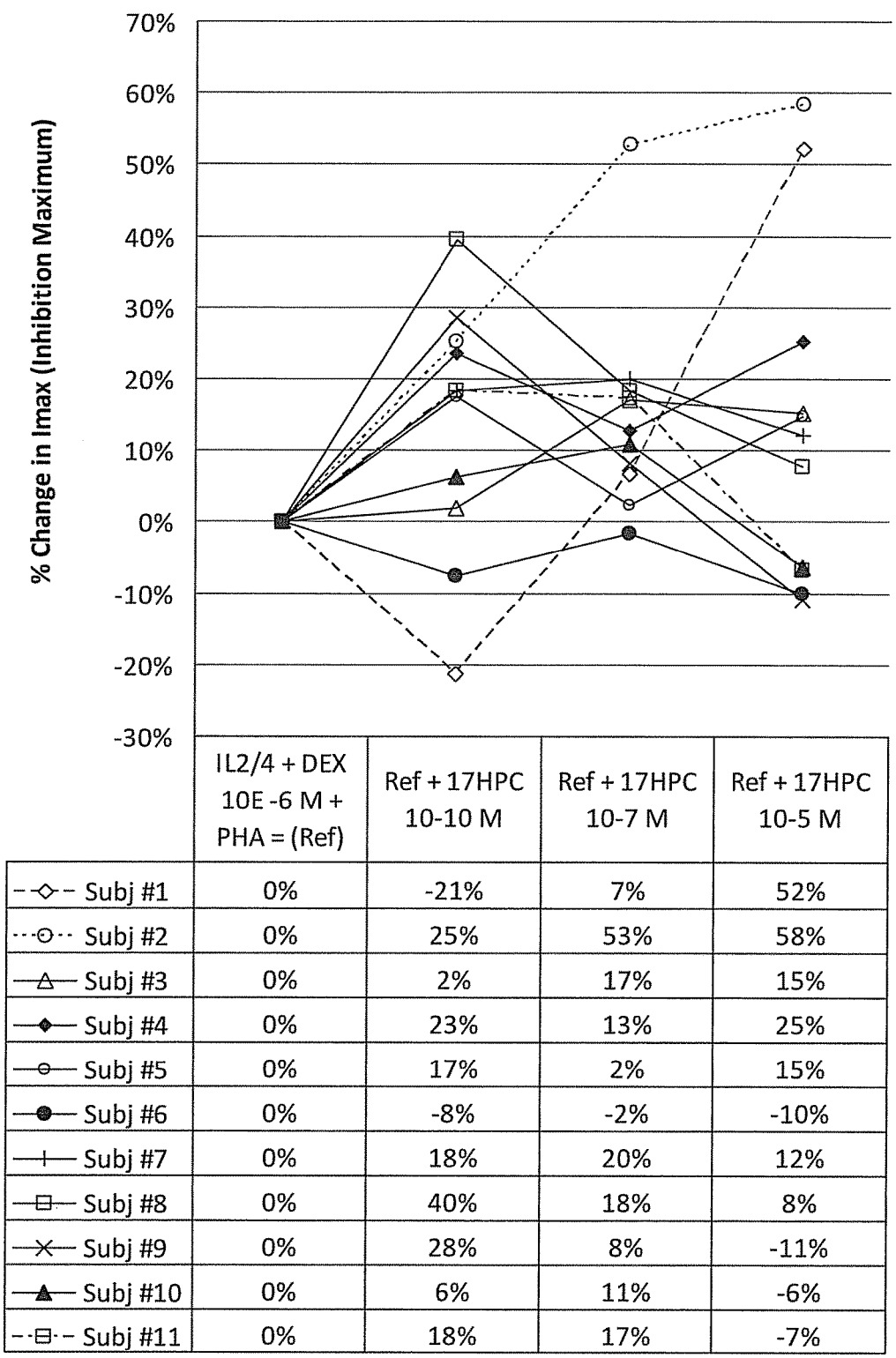
Figure 7:
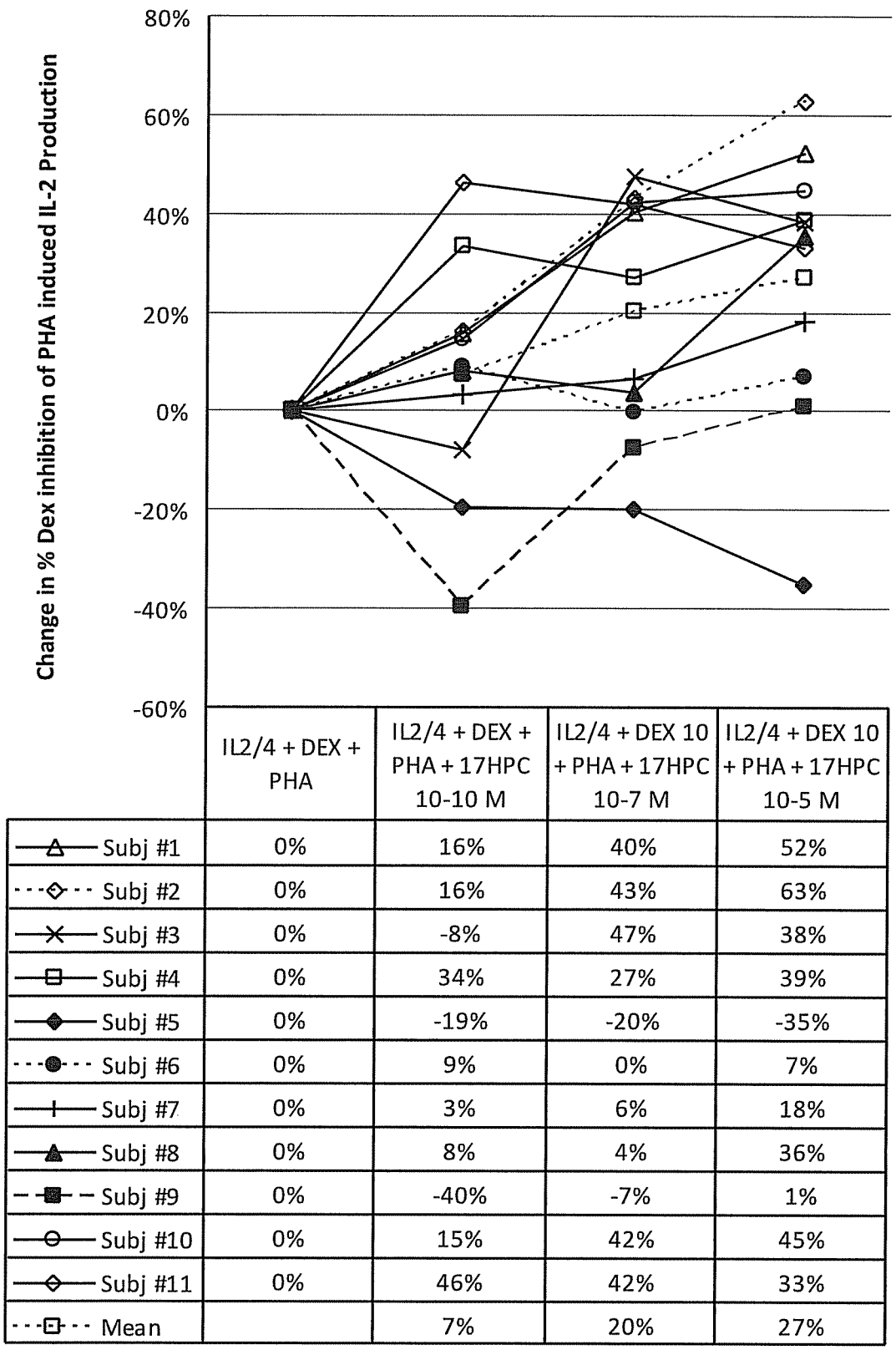

The results depicted in FIG. 7 show that 9 out 11 subjects had a more than 10% improvement in maximal Dexamethasone inhibition after receiving a dose of 17HPC, which is consistent with the results presented in FIG. 6.

Figure 8:
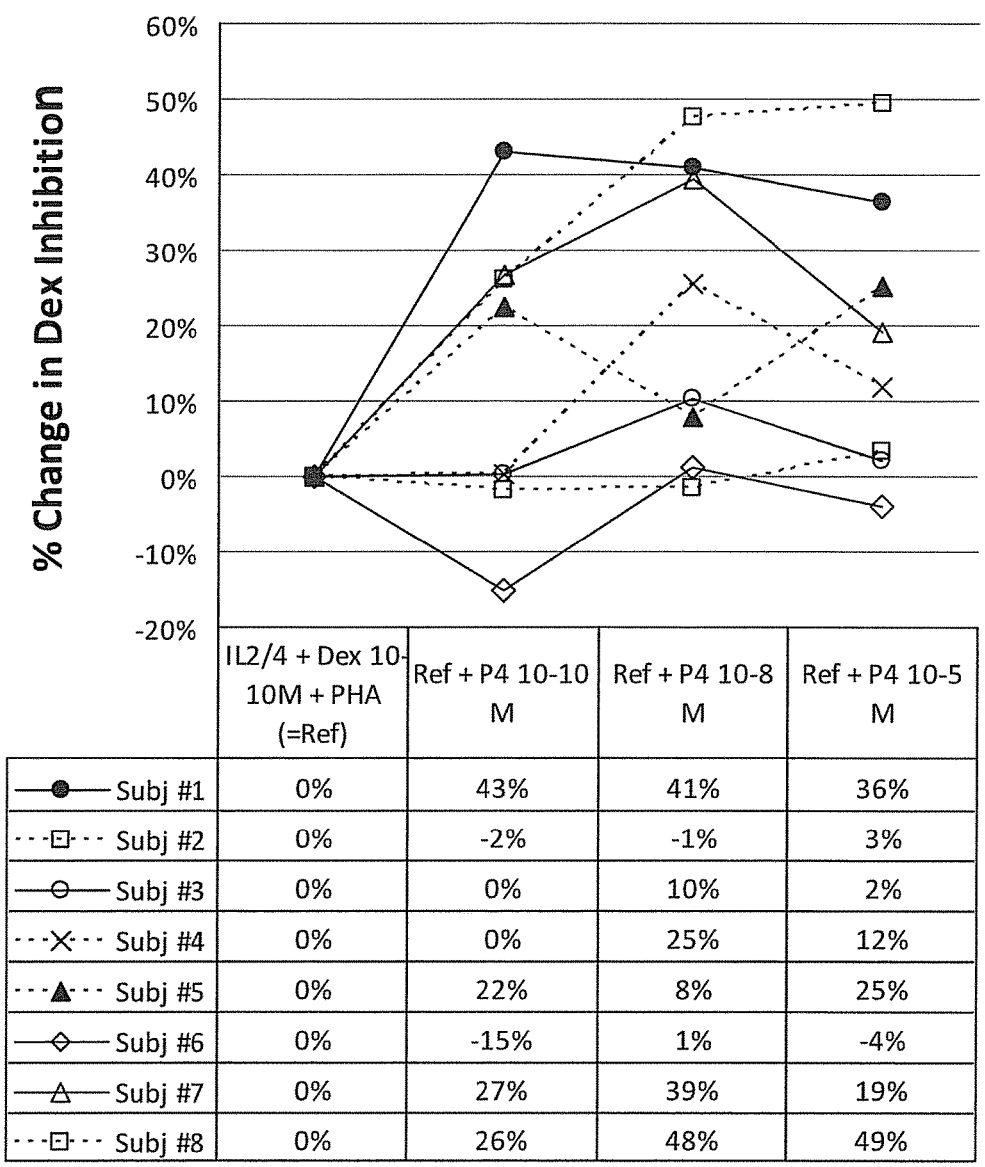

The results depicted in FIG. 8 show that 6 out of 8 subjects had a more than 10% improvement in maximal Dexamethasone inhibition after receiving a dose of natural progesterone, which is similar to 17HPC.

Figure 9:
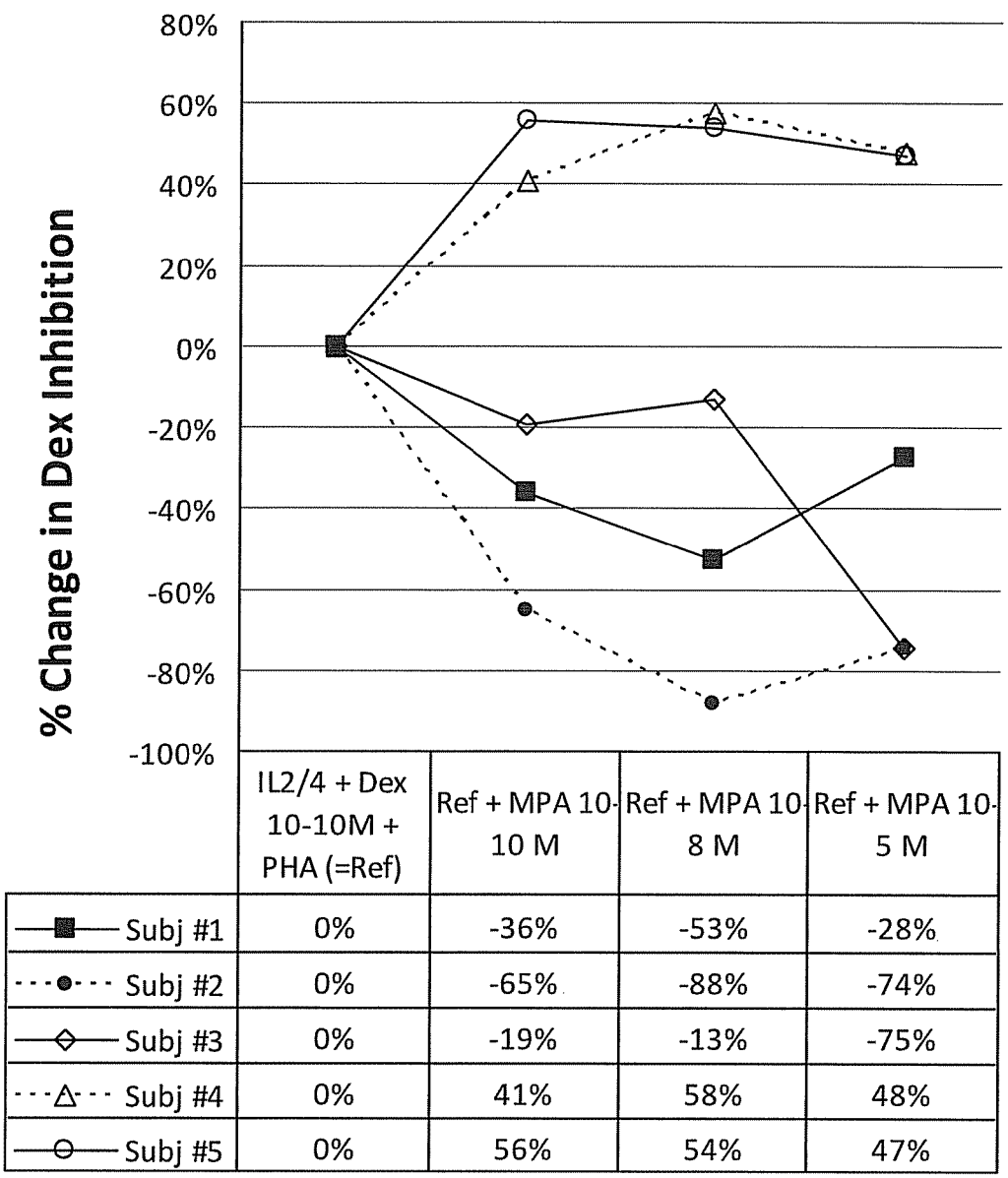

The results depicted in FIG. 9 shows that MPA treatment leads a total different response pattern: a "split" response. A sub-group had a great improvement up to 58% while another sub-group presented with a worsening in corticosteroid sensitivity, a reduction up to 88%.

Figure 10:
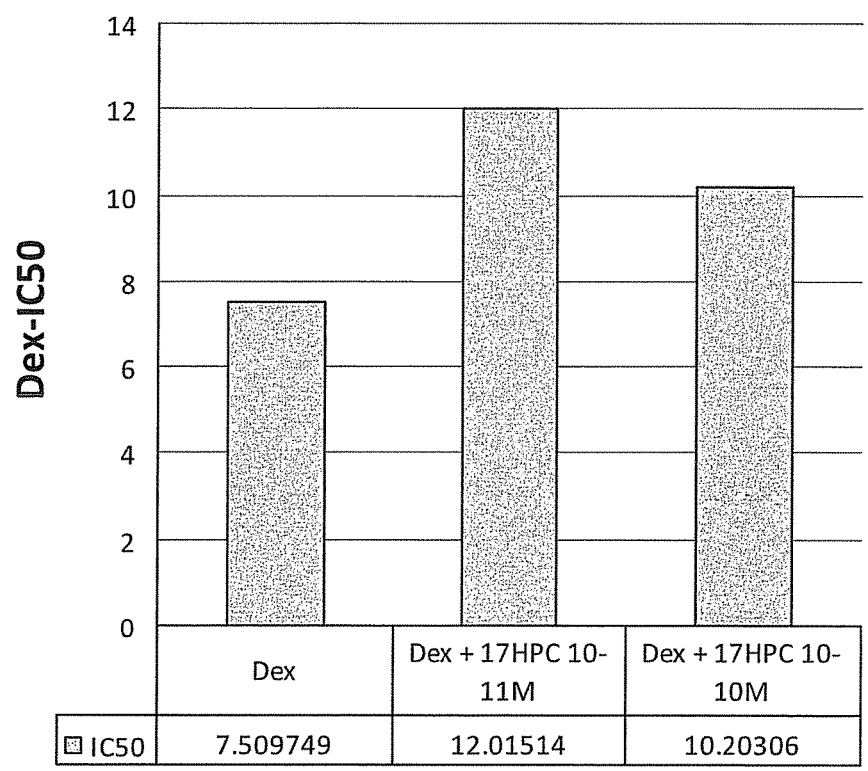

The effects of 17HPC on dexamethasone sensitivity measured by IL-2 inhibition in smokers are shown in Table 1 and FIG. 10. FIG. 10 shows add-on effect of 17HPC is improvement of steroid sensitivity.

Figure 11:
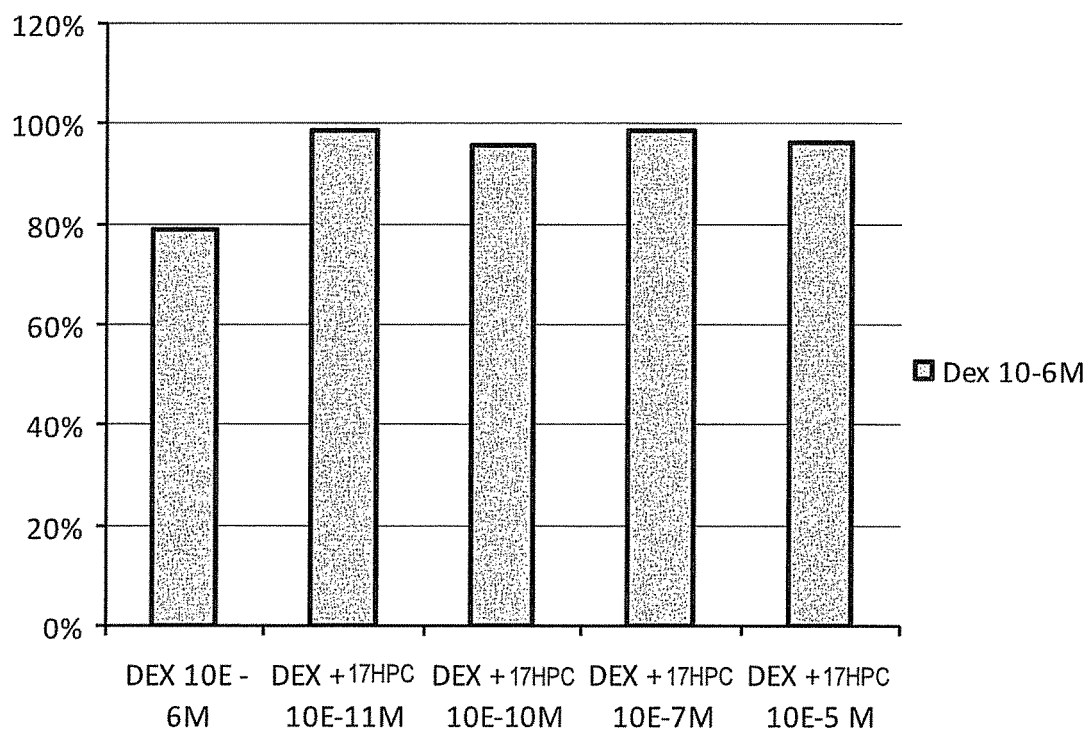

The maximal anti-inflammatory effect of Dexamethasone is 78% inhibition of PHA-induced IL-2 production at $10^{-6}$ M. The 'add-on' treatment of 17HPC produces a significantly better responsiveness and results in near 100% suppression of PHA induced IL-2 (FIG. 11). FIG. 11 thus depicts a better treatment responsiveness with the 17HPC add-on.

Figure 12:
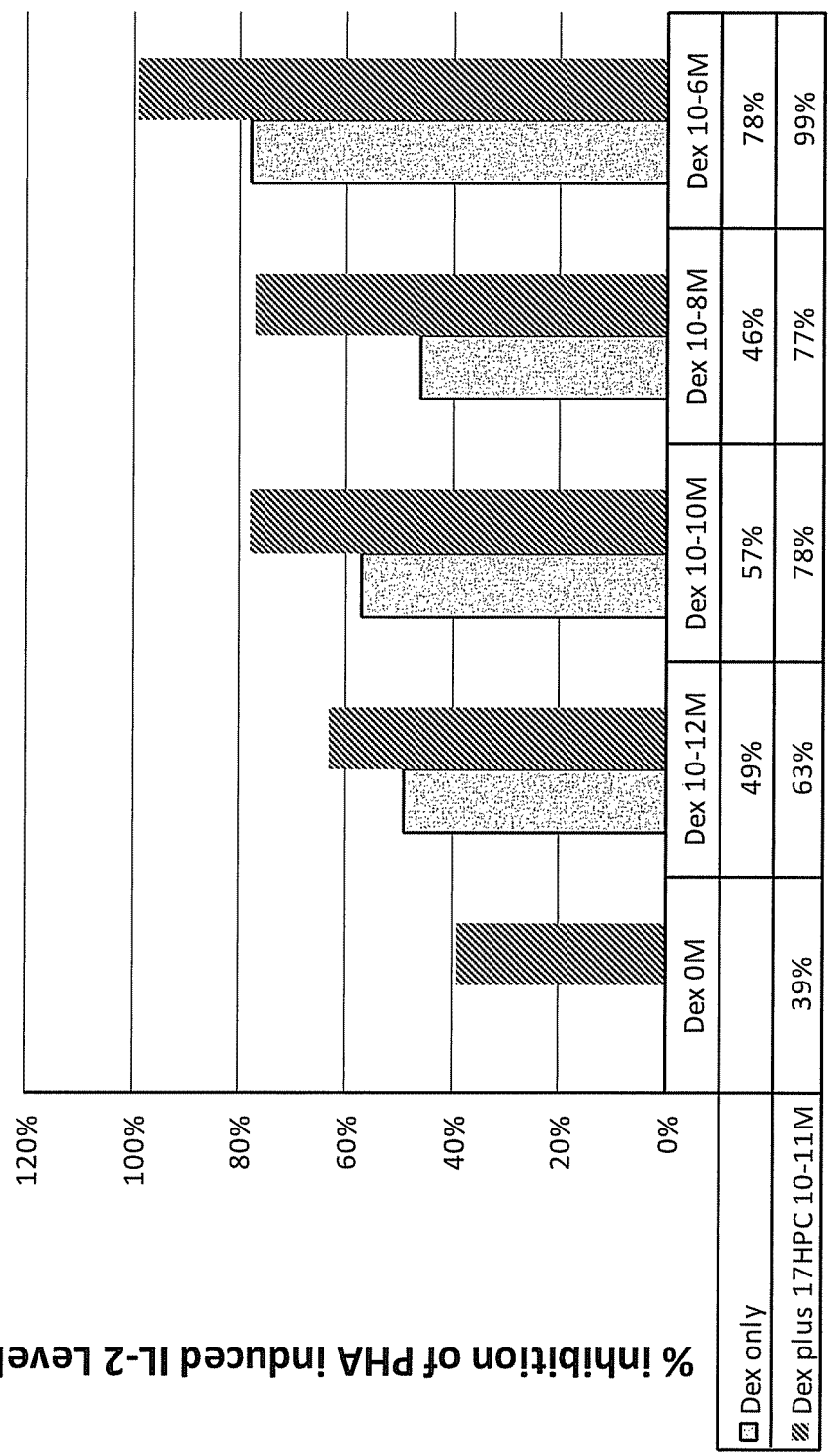

The combination of 17HPC with Dexamethasone consistently increases dexamethasone's anti-inflammatory effects, and is better than their uses individually. FIG. 12 shows that the combination leads to a synergetic effect, with 25-37% improvements in Dexamethasone efficacy. FIG. 12 thus depicts synergetic effects of combination of 17HPC with Dexamethasone.

DETAILED DESCRIPTION OF THE PREFERRED EMBODIMENTS

Described herein are preferred methods, compositions, and kits according to the present invention which are suitable for restoring corticosteroid sensitivity, enhancing glucocorticoid sensitivity and/or reversing the glucocorticoid insensitivity in a subject experiencing corticosteroid dependence or corticoid resistance or unresponsiveness or intolerance to corticosteroids. Glucocorticoid insensitivity related conditions include, for instance, a range of immune-inflammatory disorders/diseases treated with steroids when the therapy fails to achieve disease control or is not effective or intolerant or dependent or resistant to corticosteroids, and combinations thereof. More specifically, the methods, compositions, and kits of the present invention are effective to achieve the glucocorticoid-sensitizer effects of steroid-sparing in corticosteroid-dependent patients, better responsiveness or tolerance to corticosteroids, achieving efficacy by using a lower dose of corticosteroid, preventing individuals at risk for developing corticosteroid refractory responses or resistance or exacerbations in response to antigen exposures, infections, exercise, or irritants, achieving optimal immune-functions, easier responses for the subject or patient when steroid administration is tapered or withdrawn, or in prolonged administration of corticosteroids, decreased risks for developing corticosteroid-related adverse events such as opportunistic infections and bone loss, and combinations thereof. More specifically, glucocorticoid insensitivity related conditions include various conditions/disorders associated with and/or attributed to glucocorticoid resistance, glucocorticoid refractory responses, corticosteroid dependence and corticosteroid intolerance. A primary risk factor in developing glucocorticoid insensitivity is oxidative stress.

Despite the serious consequences of glucocorticoid insensitivity, there has been limited success in the treatment of subjects who suffer from various conditions/disorders associated with and/or attributed to glucocorticoid resistance, glucocorticoid refractory responses, corticosteroid dependence and corticosteroid intolerance. Calcineurin inhibitors and methotrexate may be useful in a few selected conditions, but they have not proven to be effective in most glucocorticoid insensitivity related conditions. Moreover there are significant adverse events associated with their uses. Significant toxicity and side-effects have also hampered the drug development programs for p38 MAP-kinase inhibitors, selective inhibitors to block inhibition of NFκB kinase and Phosphodiesterase-4 inhibitors. The majority of glucocorticoid insensitivity disorders don't have any association with menstrual cycle, and most subjects suffering from glucocorticoid insensitivity disorders don't experience menstrual cycle-related exacerbation, including allergy to progesterone. Advantageously in accordance with the present invention, the methods detailed herein are believed to significantly restore corticosteroid sensitivity in a subject preferably having no history of menstrual cycle-related exacerbation. The treatments and methods of the present invention have been surprisingly determined to reverse the glucocorticoid insensitivity and/or enhance glucocorticoid sensitivity in subjects suffering from at least one condition/disorder associated with and/or attributed to glucocorticoid resistance, glucocorticoid refractory responses, corticosteroid dependence and corticosteroid intolerance. Thus, the methods of the present invention are suitable for achieving the glucocorticoid-sensitizer effects of steroid-sparing in corticosteroid-dependent patients, better responsiveness or tolerance to corticosteroids, achieving efficacy by using a lower dose of corticosteroid, preventing individuals at risk for developing corticosteroid refractory responses or resistance or exacerbations in response to antigen exposures, infections, exercise, or irritants, achieving optimal immune-functions, easier responses when steroid administration is tapered or withdrawn, or in prolonged administration of corticosteroids, and decreased risks for developing corticosteroid-related adverse events such as opportunistic infections and bone loss. Preferably, the methods of the present invention are suitable for substantially negating the effect of at least one risk factor or underlying mechanism associated with glucocorticoid insensitivity. Thus, various embodiments of the present invention are directed to methods for reversing the glucocorticoid insensitivity in a subject preferably having no history of menstrual cycle-related exacerbation and suffering from one or more glucocorticoid insensitivity related conditions. In these and various other embodiments, the subject to be treated is either male or female, and of any age. Various other embodiments are directed to treating subjects that either have their first or already experienced repeated disease attacks without menstrual cycle-related exacerbation.

Although progesterone has anti-inflammatory properties trials of progesterone for inflammatory disorders such as rheumatoid arthritis have generally failed to demonstrate an effective and reproducible method for symptom control or better clinical outcomes. Subjects exhibiting a glucocorticoid-resistant or refractory response are a subset of the disease population, but a well-defined, "difficult to treat" subpopulation. For example, 20-30% of patients with severe and steroid-resistant Crohn's Disease will not respond to steroid therapy. One of the preferred objectives of the present invention is to use progesterone for treating a glucocorticoid-resistant or refractory condition demonstrated by steroid-sparing in corticosteroid-dependent patients, better responsiveness or tolerance to corticosteroids, achieving efficacy by using a lower dose of corticosteroid, preventing individuals at risk for developing refractory responses or resistance or exacerbations in response to antigen exposures, infections, exercise, or irritants, achieving optimal immune-functions, easier responses for the subject when steroid administration is tapered or withdrawn, or in or after prolonged administration of corticosteroids, decreased risks for developing corticosteroid-related adverse events such as opportunistic infections and bone loss, and combinations thereof. Furthermore, MAPK activation is a critical event that leads to corticosteroid-insensitivity. It has been reported that progesterone increases MAPK activity (Ruzycky A L. Effects of 17 beta-estradiol and progesterone on mitogen-activated protein kinase expression and activity in rat uterine smooth muscle. Eur J Pharmacol. 1996 Apr. 11; 300(3):247-54). Without being bound to a particular theory, it is currently believed that a skilled artisan would expect that MAPK activation induces a loss of GR nuclear translocation and function, leading to the development of corticosteroid-insensitivity related conditions. Again, without being bound to a particular theory, it is further currently believed that a skilled artisan would expect that the increased MAPK by progesterone would aggravate corticosteroid-insensitivity. However, in accordance with the present invention it has been surprisingly and unexpectedly discovered that the molecular effects of increased MAPK by progesterone do not interfere with the effectiveness of progesterone in treating a glucocorticoid-resistant or refractory condition. It has further been surprisingly and unexpectedly discovered that administration of progesterone such as 17alpha12 hydroxyprogesterone caproate (17-HPC) to a subject with a glucocorticoid-resistant or refractory or corticosteroid-dependent condition achieves the glucocorticoid-sensitizer effects such as steroid-sparing. Thus, in accordance with the present invention, it is currently believed that administration of progesterone (e.g., 17-HPC) can significantly restore corticosteroid sensitivity, enhance glucocorticoid sensitivity and/or reverse glucocorticoid insensitivity.

In comparison to the use of progesterone for its anti-inflammatory effects, the present discovery has surprisingly identified a new function of progestogen and its uses, i.e., reversing corticosteroid insensitivity, and clearly identifies a well-defined patient population who would benefit from the treatment, i.e., patients exhibiting corticosteroid resistance, corticosteroid dependence, corticosteroid refractory responses, and/or corticosteroid intolerance. Since most glucocorticoid insensitivity related conditions occur in subjects that do not have a history of menstrual cycle-related exacerbation, the present discovery also represents a significant advance in the art.

Definitions

As noted, glucocorticoids remain the first-line treatment for a range of immune/inflammatory and allergic diseases. However, 30% of patients fail to achieve disease control at tolerable systemic doses and continue to have an increased immune response with poor clinical outcomes. The glucocorticoid insensitivity is an important factor in the pathogenesis and prognosis of many diseases. It presents considerable management problems and cost burdens to health services. As used herein, the term "glucocorticoid insensitivity" is intended to include, but is not limited to, corticosteroid resistance, corticosteroid dependence, corticosteroid refractory responses, corticosteroid intolerance, and other types of corticosteroid ineffectiveness. It has been recognized that several distinct molecular mechanisms contribute to decreased anti-inflammatory effects of glucocorticoids. Different inflammatory diseases may share similar molecular mechanisms, and a single disease may have a heterogeneity of mechanisms.

Corticosteroid resistance to the anti-inflammatory effects of corticosteroids is defined as no clinical improvement after treatment with high-dose glucocorticoid.

Corticosteroid dependence is defined as a condition that initially responds to corticosteroids but relapses quickly upon drug withdrawal or dose tapering.

Corticosteroid refractory response is defined as a condition that does not respond to an adequate induction dose of corticosteroids. It includes relatively or totally refractory responses to glucocorticoid therapy, and often needs to be controlled by add-on treatment.

Other types of corticosteroid ineffectiveness includes need for a very high dose treatment, "difficult to treat" and "do not respond well" or severe cases, and impaired in vitro and in vivo responsiveness.

Corticosteroid intolerance is defined as toxicity of the therapy and/or risks for developing corticosteroid-related adverse events such as opportunistic infections and bone loss.

Glucocorticoid sensitizer is defined as a pharmaceutical agent and product that has a function in restoring corticosteroid sensitivity, enhancing glucocorticoid sensitivity, reversing the glucocorticoid insensitivity, and protecting against loss of glucocorticoid sensitivity, and used for treating, preventing, or ameliorating one or more of the symptoms of diseases or disorders associated with glucocorticoid insensitivity (e.g., corticosteroid dependent or corticoid resistant or unresponsive or intolerant to corticosteroids). Therapeutic effects of the use of a glucocorticoid sensitizer include any, but are not limited to, steroid-sparing in corticosteroid-dependent patients, better responsiveness or tolerance to corticosteroids, achieving efficacy by using a lower dose of corticosteroid, preventing individuals at risk for developing refractory responses or resistance or exacerbations in response to antigen exposures, infections, exercise, or irritants, achieving optimal immune functions, easier responses for the subject or patient when steroid administration is tapered or withdrawn, or after prolonged administration of corticosteroids, decreased risks for developing corticosteroid-related adverse events such as opportunistic infections, bone loss, pathologic fracture, diabetes, cataract, and combinations thereof.

As used herein, the terms "treating" or "treatment" encompass either or both responsive and prophylactic measures, e.g., designed to inhibit or delay the onset of the disease or disorder, achieve a full or partial reduction of the symptoms or disease state, and/or to alleviate, ameliorate, lessen, or cure the disease or disorder and/or its symptoms. Treatment also encompasses any pharmaceutical use of the compositions of the present invention, such as use for treating a glucocorticoid insensitivity related disease or disorder or condition. Amelioration of the symptoms of a particular disorder by administration of a particular compound or pharmaceutical composition of the present invention refers to any lessening, whether permanent or temporary, lasting or transient that can be attributed to or associated with administration of the composition.

Subject is defined herein as an animal, typically a mammal, including human. As used herein, the term "patient" includes human and animal subjects.

In practicing the methods of the present invention, effective amounts of the progesterone compounds or compositions containing therapeutically effective concentrations of the compounds, which are formulated for systemic delivery, including parenteral, oral, or intravenous or pulmonary delivery, or for local or topical application, can be used for the treatment of glucocorticoid-insensitivity related diseases or disorders, or conditions, including, but not limited to, glucocorticoid resistant conditions (e.g., glucocorticoid resistant asthma, refractory rheumatoid arthritis, refractory inflammatory bowel disease, chronic obstructive pulmonary disease and acute respiratory distress syndrome, interstitial pulmonary fibrosis, and cystic fibrosis); glucocorticoid refractory conditions (e.g., refractory ulcerative colitis, children with severe Crohn disease, corticosteroid refractory asthma, desquamative interstitial pneumonia refractory to corticosteroid, refractory inflammatory myopathies, refractory myasthenia gravis, refractory pemphigus vulgaris, methotrexate-refractory RA patients, refractory nephrotic syndrome, refractory multiple sclerosis, refractory sprue-like disease, steroid-resistant sarcoidosis, refractory mucosal lesions of pemphigus vulgaris, refractory Schnitzler syndrome, resistant dermatitis of the head and neck, severe refractory atopic dermatitis, refractory Idiopathic thrombocytopenia purpura, refractory orbital myositis, refractory or recurrent lymphomas, critically ill patients with sepsis or acute respiratory distress syndrome (ARDS) and relative adrenal insufficiency); glucocorticoid dependent conditions (e.g., rosacea, polymyalgia rheumatic, giant cell arteritis, polymyositis, dermatomyositis, Kawasaki syndrome, Guillain-Barre syndrome, chronic inflammatory demyelinating polyneuropathy, multifocal motor neuropathy, Stiff man syndrome, corticosteroid dependent systemic lupus erythematosus, corticosteroid dependent multiple sclerosis, symptomatic corticosteroid dependent asthma, primary Sjogren's syndrome, systemic vasculitis, polymyositis, organ transplants, and graft-versus-host disease); and other inflammatory diseases, autoimmune diseases, hyperproliferative diseases, and other such disease when glucocorticoid-insensitivity is implicated. Exemplary of these diseases are lupus, osteoarthritis, rhinosinusitis, polyarteritis nodosa, Wegener's granulomatosis, giant cell arteritis, allergic rhinitis, urticaria, hereditary angioedema, tendonitis, bursitis, autoimmune chronic active hepatitis, cirrhosis, transplant rejection, psoriasis, dermatitis, malignancies (e.g., leukemia, myelomas, lymphomas), acute adrenal insufficiency, rheumatic fever, granulomatous disease, immune proliferation/apotosis, hypothalamic-pituitary-adrenal (HPA) axis suppression and regulation, hypercortisolemia, modulation of the Th1/Th2 cytokine balance, chronic kidney disease, spinal cord injury, cerebral edema, thrombocytopenia, Little's syndrome, Addison's disease, autoimmune hemolytic anemia, uveitis, pemphigus vulgaris, nasal polyps, sepsis, infections (e.g., bacterial, viral, rickettsial, parasitic), type II diabetes, obesity, metabolic syndrome, depression, schizophrenia, mood disorders, Cushing's syndrome, anxiety, sleep disorders, memory and learning enhancement, or glucocorticoid-induced glaucoma, atopic dermatitis, drug hypersensitivity reactions, serum sickness, bullous dermatitis herpetiformis, contact dermatitis, exfoliative erythroderma, mycosis fungoides, pemphigus, nonsuppurative thyroiditis, sympathetic ophthalmia, uveitis and ocular inflammatory conditions unresponsive to topical steroids, allergic bronchopulmonary aspergillosis, fulminating or disseminated pulmonary tuberculosis when used concurrently with appropriate chemotherapy, hypersensitivity pneumonitis, idiopathic bronchiolitis obliterans with organizing pneumonia, idiopathic eosinophilic pneumonias, idiopathic pulmonary fibrosis, pneumocystis carinii pneumonia (PCP) associated with hypoxemia occurring in an HIV(+) individual who is also under treatment with appropriate anti-PCP antibiotics, a diuresis or remission of proteinuria in nephritic syndrome, without uremia, of the idiopathic type or that due to lupus erythematosus, ankylosing spondylitis, polymyalgia rheumatic, psoriatic arthritis, relapsing polychondritis, trichinosis with neurologic or myocardial involvement, and tuberculous meningitis.

Generally, in accordance with the present invention, the methods described herein for the treatment of glucocorticoid-insensitivity related diseases or disorders, or conditions comprise administering a pharmaceutical composition comprising a steroid hormone. Typically, the lipophilic gonadal steroid hormone is a progestogen. The progestogen may be a naturally occurring progestogen or a synthetic progestogen (i.e., a progestin). Progestogens that can be used in accordance with the present invention are grouped into the following categories: progesterone, retroprogesterone, progesterone derivative, 17α-OH progesterone derivatives (both pregnanes and norpregnanes), 19-norprogesterone derivatives, 19-nortestosterone derivatives (both estranges and gonanes), and spironolactone derivatives. Generally, the progestogen for use in accordance with the present invention is selected from the group consisting of progesterons and their derivatives or active metabolites. Specific examples of progestogens that may be used in the methods and kits of the present invention include, but are not limited to, 17alpha-HPC hydroxyprogesterone, natural progesterone, dydrogesterone, medrogestone, medroxyprogesterone, megestrol acetate, chlormadinone acetate, cyproterone acetate, gestonorone caproate, nomegestrol acetate, demegestone, promegestone, nestorone, trimegestone, norethisterone acetate, norethisterone, lynestrenol, ethynodiol diacetate, norgestrel, levonorgestrel, desogestrel, etonogestrel (3-ketodesogestrel), gestodene, norgestimate, norelgestromin (17-deacetyl norgestimate), dienogest, drospirenone, norethynodrel, norgestrel, desogestrel, etonogestrel, 19-nortestosterone, dienogest, norethynodrel, cyproterone acetate, tibolone, 19-norprogesterone, and drospirenone.

Other agents that can be used in accordance with the methods and kits of the present invention include, for example, any pharmaceutically-acceptable progestogen derivatives, i.e., derivatives of 17alpha-HPC hydroxyprogesterone, natural progesterone, dydrogesterone, medrogestone, medroxyprogesterone, megestrol, chlormadinone, cyproterone, gestonorone caproate, nomegestrol acetate, demegestone, promegestone, nestorone, trimegestone, norethisterone, norethisterone, lynestrenol, ethynodiol diacetate, norgestrel, levonorgestrel, desogestrel, etonogestrel (3-ketodesogestrel), gestodene, norgestimate, norelgestromin (17-deacetyl norgestimate), dienogest, drospirenone, norethynodrel, norgestrel, desogestrel, etonogestrel, 19-nortestosterone, dienogest, norethynodrel, cyproterone, tibolone, 19-norprogesterone, and drospirenone. Each progestogen can be derivatized as the corresponding salts, esters, enol ethers or esters, acids, bases, solvates, hydrates or prodrugs prior to formulation, as described herein. Representative pharmaceutically-acceptable salts include, but are not limited to, amine salts, such as but not limited to, chloroprocaine, choline, ammonia, diethanolamine and other hydroxyalkylamines, ethylenediamine, Nmethylglucamine, procaine, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc, aluminum, and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. For example, the organic acid of acetates is often used such as megestrol acetate, chlormadinone acetate, cyproterone acetate, gestonorone caproate, nomegestrol acetate, and cyproterone acetate.

Additional representative agents that can be used in accordance with the methods and kits of the present invention include, for example, any progestogen active metabolite including, but not limited to, active metabolites of 17alpha-HPC hydroxyprogesterone, natural progesterone, dydrogesterone, medrogestone, medroxyprogesterone, megestrol acetate, chlormadinone acetate, cyproterone acetate, gestonorone caproate, nomegestrol acetate, demegestone, promegestone, nestorone, trimegestone, norethisterone acetate, norethisterone, lynestrenol, ethynodiol diacetate, norgestrel, levonorgestrel, desogestrel, etonogestrel (3-ketodesogestrel), gestodene, norgestimate, norelgestromin (17-deacetyl norgestimate), dienogest, drospirenone, norethynodrel, norgestrel, desogestrel, etonogestrel, 19-nortestosterone, dienogest, norethynodrel, cyproterone acetate, tibolone, 19-norprogesterone, and drospirenone. For example, active metabolites of progesterone include allopregnanolone and 5alphapregnan-3,20-dione the active metabolite. Active metabolites of 17-HPC include M13 monohydroxy-; M12, monohydroxy-; M19, monohydroxy-; M7, dihydroxy-; and M16, monohydroxy-.

In various embodiments, another group of steroid hormone, glucocorticoids, for use in accordance with the present invention is preferably selected from the group consisting of naturally produced steroid hormones, or synthetic compounds, that inhibit the process of inflammation. Specific examples of glucocorticoids include, but are not limited to, hydrocortisone (cortisol), cortisone acetate, dexamethasone (hereinafter, "Dexamethasone"), prednisone, prednisolone, methylprednisolone, betamethasone, triamcinolone, beclometasone, Paramethasone, fluticasone, fludrocortisone acetate, deoxycorticosterone acetate (DOCA), Fluprednisolone, fluticasone propionate, budesonide, beclomethasone dipropionate, flunisolide and triamcinolone acetonide.

In practicing the methods of the present invention, effective amounts of the compounds or compositions containing therapeutically effective concentrations of the compounds, are preferably formulated for systemic delivery, including parenteral, oral, or intravenous delivery, or for local or topical application. For example, the pharmaceutical composition may be administered by subcutaneous, intravenous, intraperitoneal, intraarterial or intramuscular injection; rectally; by transdermally delivery; intravaginal delivery; or buccally; or by oral delivery. When administered by subcutaneous or intramuscular injection, the steroid hormone is suitably formulated as a depot formulation to allow for sustained release of the steroid hormone over an extended period of time. When administered by topical administration, including intravaginal delivery, delivery may suitably be, for example, via a solution, suspension, emulsions or the like and are preferably formulated as creams, gels, ointments, emulsions, solutions, elixirs, lotions, suspensions, tinctures, pastes, foams, aerosols, irrigations, sprays, suppositories, bandages, dermal patches or any other formulations suitable for the route. When an inhalation route of administration is used, delivery may preferably be, for example, via an aerosol spray or powder mixture in a pressurized pack or a nebulizer or in an inhaler.

With respect to the frequency of administration, any frequency which achieves the desired result (i.e., steroid-sparing in corticosteroid-dependent patients, better responsiveness or tolerance to corticosteroids, achieving efficacy by using a lower dose of corticosteroid, preventing individuals at risk for developing refractory responses or resistance or exacerbations in response to antigen exposures, infections, exercise, or irritants, achieving optimal immune-functions, easier responses for the subject when steroid administration is tapered or withdrawn, or after prolonged administration of corticosteroids, decreased risks for developing corticosteroid-related adverse events such as opportunistic infections and bone loss, and combinations thereof, may be used. The frequency of administration will preferably be determined, at least in part, by the steroid hormone(s) and/or dosage form selected. In various embodiments, the pharmaceutical composition is preferably administered at an interval exceeding daily or once per week. For example, the pharmaceutical composition may be administered once every other week, once monthly, once every two months, or once every three months. In various other embodiments, the pharmaceutical composition is administered once weekly, or at an interval of less than one week (e.g., daily or every other day). For example, when the steroid hormone is 17alpha-hydroxyprogesterone caproate (17-HPC), administration may suitably be via daily, once-weekly or once every two-week, or once-monthly or once every 3-month injections. Those skilled in the art will understand that the route of administration and frequency of administration for the pharmaceutical compositions used in the methods and kits of the present invention will depend on a variety of factors including, for example, the particular steroid hormone(s) used, the formulation in which it is delivered, the tissue being treated, the age and gender of the individual treated, in vivo or in vitro test data, and the professional judgment of the particular patient's needs. The dosing frequency ranges set forth herein are exemplary only and are not intended to limit the scope or practice of formulations provided herein.

The skilled artisan will also appreciate that appropriate dosing of the steroid hormone will depend on the steroid hormone(s) selected, the route of administration and dosage form, the frequency of administration, the disease(s) to be treated, the metabolic stability and length of action of that compound, the species, age, body weight, general health, and diet of the subject, rate of excretion, drug combination, and severity of the particular condition. The effective amount of a steroid hormone provided herein can be determined by one of ordinary skill in the art, and includes exemplary dosage amounts for a mammal of from about 0.001 to 100 mg/kg of body weight of active compound given orally per day. For example, to achieve the endometrium and antigonadotropic effects (i.e., dose for ovulation inhibition), 0.15 mg/day p.o. for Levonorgestrel or Desogestrel is preferably desired while the required amount is much higher, 5-10 mg/day for Medroxyprogesterone acetate or 200-300 mg/day for Progesterone.

The skilled artisan will also appreciate that appropriate dosing of the steroid hormone will depend on gender as progestogen is the sex hormone. Progesterone is primarily secreted by the granulosa cells and the corpus luteum in the ovary. During pregnancy, a major source of progesterone also comes from the placenta. Males produce progesterone in the adrenal gland and testes, as this is a precursor of testosterone. In women, progesterone levels are relatively low during the preovulatory phase of the menstrual cycle, rise after ovulation, and are elevated during the luteal phase. Progesterone levels tend to be <2 ng/ml prior to ovulation, and >5 ng/ml after ovulation. If pregnancy occurs, progesterone levels are initially maintained at luteal levels. With the onset of the luteal-placental shift in progesterone support of the pregnancy, levels start to rise further and may reach 100-200 ng/ml at term. The reference range for progesterone levels in adult men is 0.13-0.97 ng/ml. Adult males have levels similar to those in women during the follicular phase of the menstrual cycle as well as the level in postmenopausal women. Clearly, women regularly experience a 17-fold change in serum progesterone concentration during the menstrual cycle, or more than 100-fold increase in pregnancy. Thus, tolerance or maximum dose or minimal effective dose of progestogen treatment would be higher in women than in males. For example, when the steroid hormone is 17alpha-hydroxyprogesterone caproate (17-HPC) and a common dosage used is 150-500 mg weekly injection for its uses in women-health related indications. Given some important effects of progesteron on restoring corticosteroid sensitivity are assumed to be mediated non-genomically through different molecular biological modes of action (i.e., functions not related to progestational activity), this may result in some pharmacodynamic variability. A much lower or higher dose of progesterone (e.g. 17-HPC) may be selected as well as a different dosage level for male subjects. The dosing ranges set forth herein are exemplary only and are not intended to limit the scope or practice of formulations provided herein.

Preferably, the pharmaceutical compositions of the present invention contain: i) a physiologically acceptable carrier, diluent, or excipient, or a combination thereof; and ii) one or more steroid hormone(s) as described herein. The compositions can be formulated for single dosage administration or for multiple dosages. Dosage forms or compositions containing steroid hormone(s) in the range of 0.005% to 100% with the balance made up from non-toxic carrier can be prepared. For example, the pharmaceutical composition may contain one or more diluents, one or more carriers, one or more binders, one or more coatings, one or more lubricants, one or more solvents, one or more buffers, one or more preservatives, one or more flavoring agents, one or more dyes, and/or one or more absorption enhancers, and/or one or more biodegradable polymers. The particular excipient(s) included in the pharmaceutical composition will depend on the particular steroid hormone(s) and dosage form selected, and the skilled artisan will be able to readily select appropriate excipients once the steroid hormone(s) and the dosage form therefore have been chosen. For example, for oral administration, a pharmaceutically acceptable non-toxic composition can be formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions preferably include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. For another example, conventional injectables can be prepared in conventional forms, either as liquid solutions or suspensions, solid forms suitable for solution or suspension in liquid prior to injection, or as emulsions. Suitable excipients include, for example, water, saline, dextrose, glycerol, mannitol, 1,3-butanediol, Ringer's solution, an isotonic sodium chloride solution or ethanol. For another example, injectable suspensions are prepared using appropriate liquid carriers, suspending agents and the like. Certain pharmaceutical compositions for injection are presented in unit dosage form, e.g., in ampules or in multi dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes.

In addition to administration of a progestogen hormone, the methods of the present invention may further comprise one or more additional therapies aimed at the treatment of glucocorticoid insensitivity related diseases or disorders, or conditions, as discussed herein. The one or more additional treatments may include, for example, glucocorticoid (e.g., hydrocortisone, cortisone acetate, dexamethasone, prednisone, prednisolone, methylprednisolone, betamethasone, triamcinolone, beclometasone, Paramethasone, fluticasone, fludrocortisone acetate, deoxycorticosterone acetate, Fluprednisolone, fluticasone propionate, budesonide, beclomethasone dipropionate, flunisolide and triamcinolone acetonide, an androgen (e.g., dehydroepiandrosterone (DHEA)), an estrogen (e.g., estradiol), immunosuppressive or immunomodulators agents (e.g., cyclosporine, methotrexate, gold, 6-mercaptopurine, biologic products such as infliximab, etanercept, and adalimumab, intravenous immunoglobulin and Mepolizumab), and calcineurin inhibitors (e.g., ciclosporin, tacrolimus), p38 MAP kinase inhibitors, JNK inhibitors (decrease API), Vitamin D, MIF inhibitors, Histone deacetylate-2 activators, Theophylline, Phosphoinositide-3-kinase-δ inhibitors, leukotriene modifiers, long-acting beta agonists, antioxidants, iNOS inhibitors and P-glycoprotein inhibitors, and combinations thereof. The above other pharmaceutical agents, when employed in combination with the agents described herein, can be used, for example, in those amounts indicated in the Physicians' Desk Reference (PDR) or as otherwise determined by one of ordinary skill in the art. The amount of an agent used with non-oral routes is preferably determined based upon corresponding serum concentration level of an oral dosage or containing a quantity of the active compound in an amount sufficient to alleviate the symptoms of the treated subject. In the methods provided herein, such other pharmaceutical agent(s) can be administered prior to, simultaneously with, or following the administration of the compounds provided herein. Therapeutic effects of the use of a glucocorticoid sensitizer include any, but not limited to, dosing-sparing of concurrent treatment drugs above, better responsive or tolerant to concurrent treatment drugs, achieving efficacy by using lower dose of concurrent treatment drugs, preventing individuals at risk for developing refractory responses or resistance of concurrent treatment drugs, achieving optimal immune-functions, easier responses after tapering or withdrawal of concurrent treatment drugs, or prolonged administration of concurrent treatment drugs, decreased risks for developing drug-related adverse events due to concurrent treatment drugs, and combinations thereof. Examples 1-2 demonstrate the establishment of study models in evaluating steroid sensitivity and steroid resistance, i.e., PHA-induced IL-2 production and IL-2/4 induced steroid resistance in human peripheral blood mononuclear cells (PBMCs) from healthy male smokers.

Examples 1 and 2 demonstrate the establishment of study models in evaluating steroid sensitivity and steroid resistance, i.e., PHA-induced IL-2 production and IL-2/4 induced steroid resistance in human peripheral blood mononuclear cells (PBMCs) from healthy male smokers.

Examples 3, 4 and 5 demonstrate that progestogen reverses corticosteroid resistance and improves corticosteroid sensitivity under a steroid-resistant condition (i.e., IL-2/4 induced).

Examples 6, 7 and 8 demonstrate that progestogen improves corticosteroid sensitivity under a non-steroid-resistant condition (i.e., PHA-induced IL-2 production without adding IL-2/4).

It has been surprisingly discovered, in accordance with the present invention, that the effects of the use of a glucocorticoid sensitizer include, but are not limited to, steroid-sparing in corticosteroid-dependent patients, better responsiveness or tolerance to corticosteroids, achieving efficacy by using a lower dose of corticosteroid, preventing individuals at risk for developing refractory responses or resistance or exacerbations in response to antigen exposures, infections, exercise, or irritants, achieving optimal immune-functions, easier responses for a patient when steroid administration is tapered or withdrawn, or prolonged administration of corticosteroids, decreased risks for developing corticosteroid-related adverse events such as opportunistic infections, bone loss, pathologic fracture, diabetes, cataract, and combinations thereof.

In Vitro Screening Materials and Methods
Overview

IL-2/4 induced steroid resistance in human peripheral blood mononuclear cells (PBMCs) is a well-recognized study model to evaluate potential modifiers of steroid resistance and sensitivity (Kam, J. C. etc. *Combination IL-2 and IL-4 reduces glucocorticoid receptor-binding affinity and T cell response to glucocorticoids. J. Immunol* 1993. 151: 3460-3466. Irusen, E. etc. *p38 mitogen-activated protein kinase-induced glucocorticoid receptor phosphorylation reduces its activity: role in steroid-insensitive asthma. J Allergy Clin. Immunol* 2002. 109: 649-657. Creed T J etc. *The Effects of Cytokines on Suppression of Lymphocyte Proliferation by Dexamethasone. J Immunol* 2009; 183; 164-171). The dexamethasone inhibition of lymphocyte proliferation and cytokine assay correlates well with the outcome of steroid therapy in patients with inflammatory diseases. The suppression of cytokine releases by dexamethasone (also referred to herein in this application as "Dexamethasone") in healthy volunteers is used to measure changes in steroid sensitivity and steroid resistance. Following PBMCs stimulation with mitogen phytohemagglutinin (PHA), there is a strong correlation between cytokine secretion levels and steroid resistance as well as steroid sensitivity in vitro. Addition of IL-2, IL-4 and TNF-reduce steroid sensitivity.

The objective of one study was to evaluate the compounds' effect on reversing corticosteroid resistance, measured by an increase in the ability of dexamethasone to inhibit PHA-induced IL-2 release in the IL-2 and IL-4 induced steroid resistant model.

The compounds' effects were assessed in improving corticosteroid sensitivity, measured by IC50 improvement, steroid-sparing, achieving a similar anti-inflammatory efficacy by using a lower dose of corticosteroid, better responsiveness and combination of synergetic effects in the PHA-induced IL-2 release in PBMCs.

Materials

PBMCs (peripheral blood mononuclear cells; PBMCs) separation system: Accuspin system-Histopaque from GEHealthcare Bio-Sciences AB (US); RPMI-1640 Medium from HyClone, Beijing China, dimethyl sulfoxide (DMSO) from Sigma (US), 17α-HYDROXYPROGESTERONE CAPROATE (17HPC) (CAS No: 630-56-8), MEDROXY-PROGESTERONE ACETATE (MPA) (CAS No. 71-58-9), natural Progesterone (P4) (CAS No. 57-83-0), Dexamethasone (Dexamethasone) (CAS No: 50-02-2) and PHA from Sigma Ltd (US); recombinant IL-2 and IL-4 from Pepro-Tech, IL-2 immunosorbent assay kit (ELISA for IL-2) from ExCell Biology, Shanghai China; anti-human anti-CD3 and anti-CD28 from R&D Systems (US).

Isolation of PBMCs

PBMCs were isolated from human blood buffy coats provided by a regional blood center. Random buffy coat cells from male donors were a by-product of blood processed for clinical use and no details (i.e., personal identification and background) were provided except for tobacco use. Almost all of the male blood donors were cigarette smokers. PBMCs were separated using a porous high density polyethylene barrier (HISTOPAQUE from GEHealthcare Bio-Sciences AB (US). After centrifugation of blood samples in each tube (35 minutes at 800×g at room temperature, or RT), PBMCs were collected and washed twice with Hank's buffered saline solution (HBSS). PBMCs were resuspended in RPMI-1640 medium containing 10% fetal calf serum (FCS) and 15 mM glutamine and cells were counted and plated.

Culture of Cells

PBMCs ($2 \times 10^6$) were incubated with or without IL-2 (13 ng/ml) and IL-4 (6.5 ng/ml) for 48 hours in RPMI-1640 medium containing 10% FCS and 2 mM glutamine. PBMCs were counted and plated again at $10^7$ cells/ml before stimulating with or without 17α-HYDROXYPROGESTERONE CAPROATE (17HPC), Progesterone (P4) and MEDROXY-PROGESTERONE ACETATE (MPA) for 12 hours prior treatment of Dexamethasone dexamethasone. IL-2 and IL-4 stimulated PBMCs were also plated at a concentration of $10^6$ cells/ml in 96-well plates ready for PHA (15 μg/mL, 24 hours) stimulation of cytokine release and detection by ELISA.

Sandwich-ELISA (Enzyme Linked Immunosorbent Assay)

PBMC Cells ($10^6$ cells/ml) were plated in 96-well plates and stimulated with or without dexamethasone ($10^{-12}$M to $10^{-6}$M) for 1 hour before transferring the cells in a 96-well plate with or without PHA (15 μg/mL) 24 hours at 37° C., 5% $CO_2$. Serial dilutions of standards and PBMCs' supernatants were measured by enzyme linked immunosorbent assay to determine IL-2 at baseline and its levels after 17HPC, P4 and MAP treatments. Optical density was measured at 450 nm and corrected with 550 nm. The concentration of IL-2 was calculated using the standard curve and taking into account the supernatant dilution used. Detection limit for IL-2 is 4.0 pg/ml.

Statistical Analysis

Data are expressed as mean±SD. The efficacies of the drug treatments were analyzed by paired t-test. One-way analysis of variance was used to compare three or more matched groups and 95% CI was performed to present groups differences. All graphs indicate mean values of results or % inhibition of PHA-stimulated IL-2. IC50 values were calculated by using a sigmoidal model (BioDataFit). A p value<0.05 was considered statistically significant.

Results

Simultaneous Measurement of Steroid Sensitivity in PBMCs ($10^6$ Cells/ml)

Figure 1:
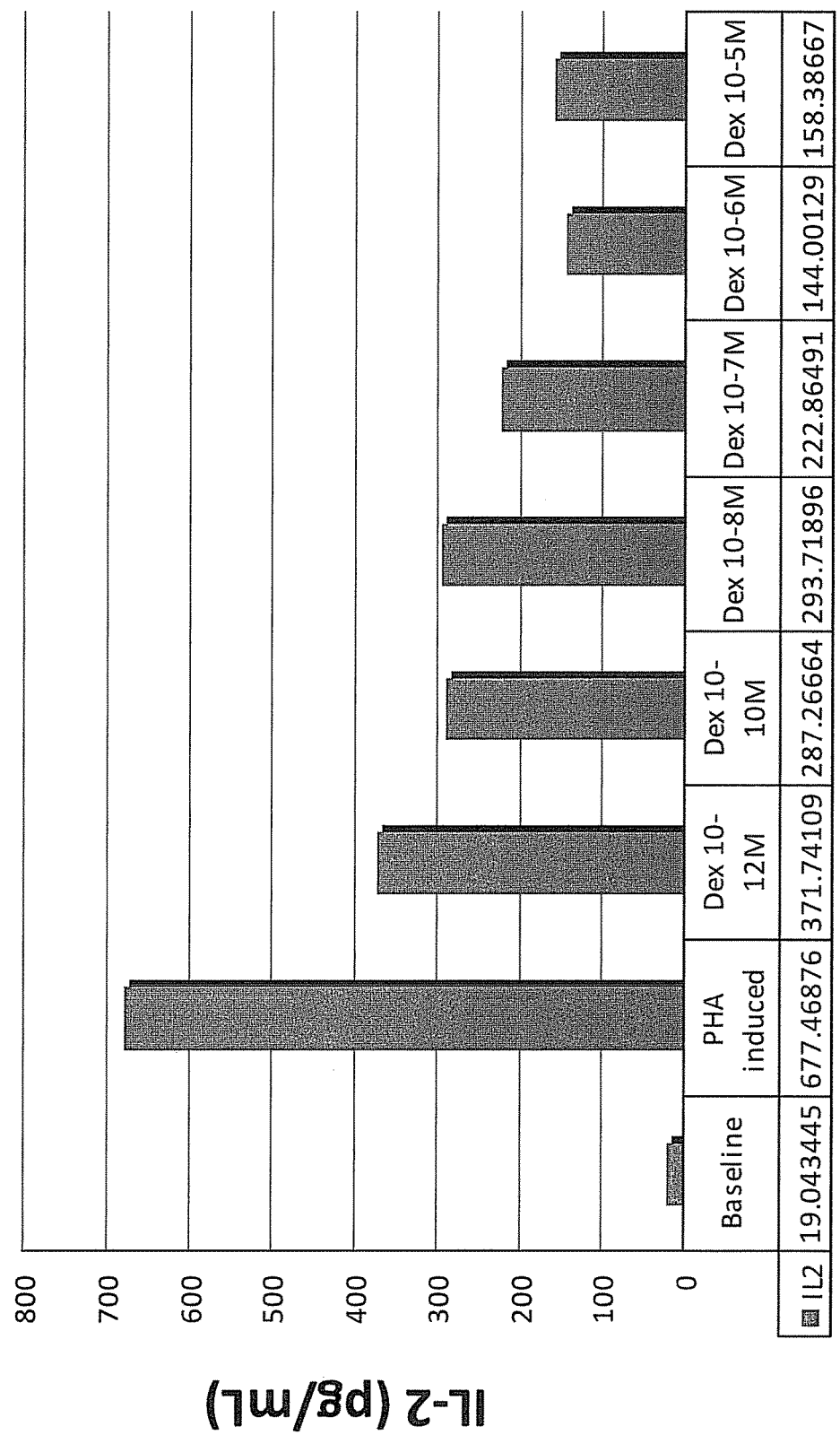
FIGS. 1-12 are graphical depictions of the results of several examples which illustrate certain embodiments of the invention, but in now way limit the scope of the invention.

To measure glucocorticoid sensitivity simultaneously, PBMCs ($10^6$ cells/ml) were plated in 96-well plates and stimulated with or without serial dilutions of dexamethasone ($10^{-12}$M to $10^{-5}$ M) for 1 hour, and then were subsequently with PHA (15 μg/mL) for 24 hours at 37° C., 5% $CO_2$. IL-2 levels were quantified using ELISA. Results in FIG. 1 include IL-2 levels at baseline, after PHA stimulation and dose-dependent inhibition of IL-2 by dexamethasone. The levels of IL-2 in PBMCs were 19±25 pg/ml at baseline in healthy Male smokers (n=11), 677±447 pg/ml after PHA stimulation PHA (n=20), 371±447 pg/ml at dexamethasone $10^{-12}$M (n=11), 287±313 pg/ml at dexamethasone $10^{-10}$ M (n=14), 293±338 pg/ml at dex $10^{-8}$M (n=17) and 144±157 pg/ml at dexamethasone $10^{-6}$M (n=17). The Dexamethasone and 17HPC treatments have no significant effect in basal IL-2 level (data not shown). FIG. 1 thus shows IL-2 levels (mean) at baseline, after PHA stimulation and effect of dexamethasone on PHA-induced IL-2 production (n=20) (p<0.001). Dexamethasone shows a significant, dose-response inhibition of IL-2 production (FIG. 1).

Example 1. Addition of IL-2 and IL-4 Reduces Steroid Sensitivity or Induces Steroid Resistance Among Male Smokers IL-2/4 induced steroid resistance in PBMCs, a well-recognized study model, was used to evaluate potential modifiers of steroid resistance and sensitivity. PBMCs from healthy smokers were collected. Corticosteroid insensitivity or resistance was induced by adding IL-2 and IL-4 in peripheral blood mononuclear cells (PBMCs) from healthy male smokers (n=11). PBMCs ($10^6$ cells/ml) stimulated with or without IL-2 (13 ng/ml) and IL-4 (6.5 ng/ml) were cultured in 96-well plates for 48 hours and subsequently being exposed serial dilutions of dexamethasone ($10^{-10}$M, $10^{-8}$M to $10^{-6}$ M) for 1 hour, and then were stimulated with PHA (15 μg/mL) for 24 hours at 37° C., 5% CO2. IL-2 levels were quantified using ELISA. Percentage of inhibition on PHA-induced IL-2 production was calculated as % Inhibition=1−(IL-2 with Dexamethasone/IL-2 without Dexamethasone).

Figure 2:
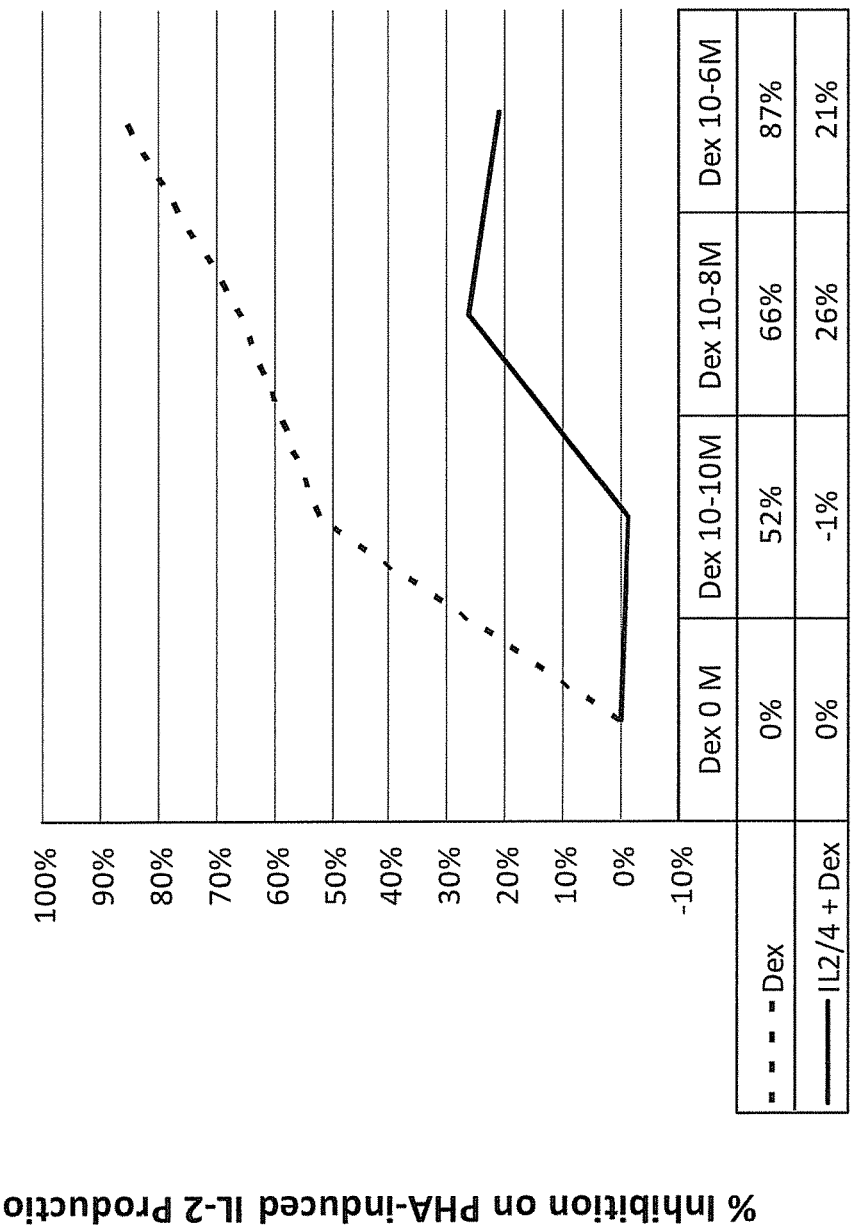

The results depicted in FIG. 2 show that inhibition ability of dexamethasone on PHA-induced IL-2 production was significantly reduced with addition of IL-2 and IL-4 among male smokers. For example, % inhibition with low dose Dexamethasone $10^{-10}$ M was completely lost: 52% vs. no inhibition, and with higher dose Dexamethasone $10^{-6}$M: 87% vs. 21%, a significant reduction. Addition of IL-2 and IL-4 reduces steroid sensitivity or induces steroid resistance among male smokers, a valid steroid-resistant model/condition.

Example 2. Progestogen Improves Corticosteroid Sensitivity or Reverses Corticosteroid Resistance Among Male Smokers Corticosteroid insensitivity or resistance can be reversed pharmacologically. We investigated the effects of progestogen drug class which is currently unknown for its function in reversing steroid resistance, and test Progestogen drugs of 17α-HYDROXYPROGESTERONE CAPROATE (17HPC), MEDROXYPROGESTERONE ACETATE (MPA) and natural Progesterone (P4) on their effects in improving glucocorticoid sensitivity in peripheral blood mononuclear cells (PBMCs) from healthy male smokers.

PBMCs ($10^6$ cells/ml) stimulated with IL-2 (13 ng/ml) and IL-4 (6.5 ng/ml) were cultured in 96-well plates for 48 hours and subsequently stimulated with 17HPC ($10^{-10}$ M, $10^{-7}$ M and $10^{-5}$ M) or P4 or MPA (($10^{-10}$ M, $10^{-8}$ M and $10^{-5}$ M) for 12 hours before being exposed with or without low and high doses of dexamethasone ($10^{-10}$M and $10^{-6}$ M) for 1 hour, and then were subsequently with PHA (15 µg/mL) for 24 hours at 37° C., 5% CO2 (n=11 for the combinations of 17HPC+Dexamethasone groups). IL-2 levels were quantified using ELISA. A 10% increase in maximal Dexamethasone inhibition (Imax) under a steroid-resistant condition represents a clinical meaningful improvement (Creed T J etc. *The Effects of Cytokines on Suppression of Lymphocyte Proliferation by Dexamethasone. J Immunol* 2009; 183; 164-171).

Figure 3:
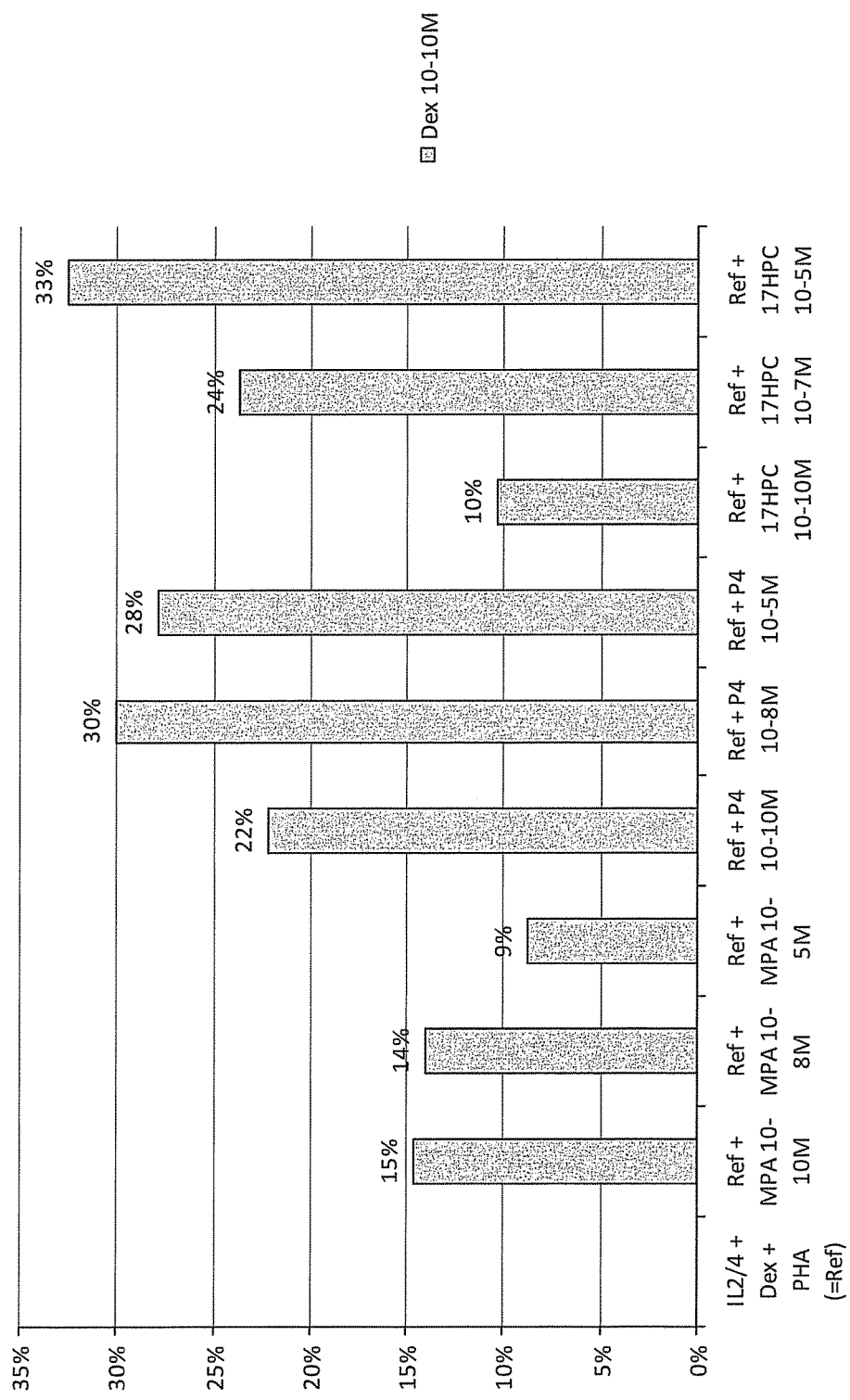
Figure 4:
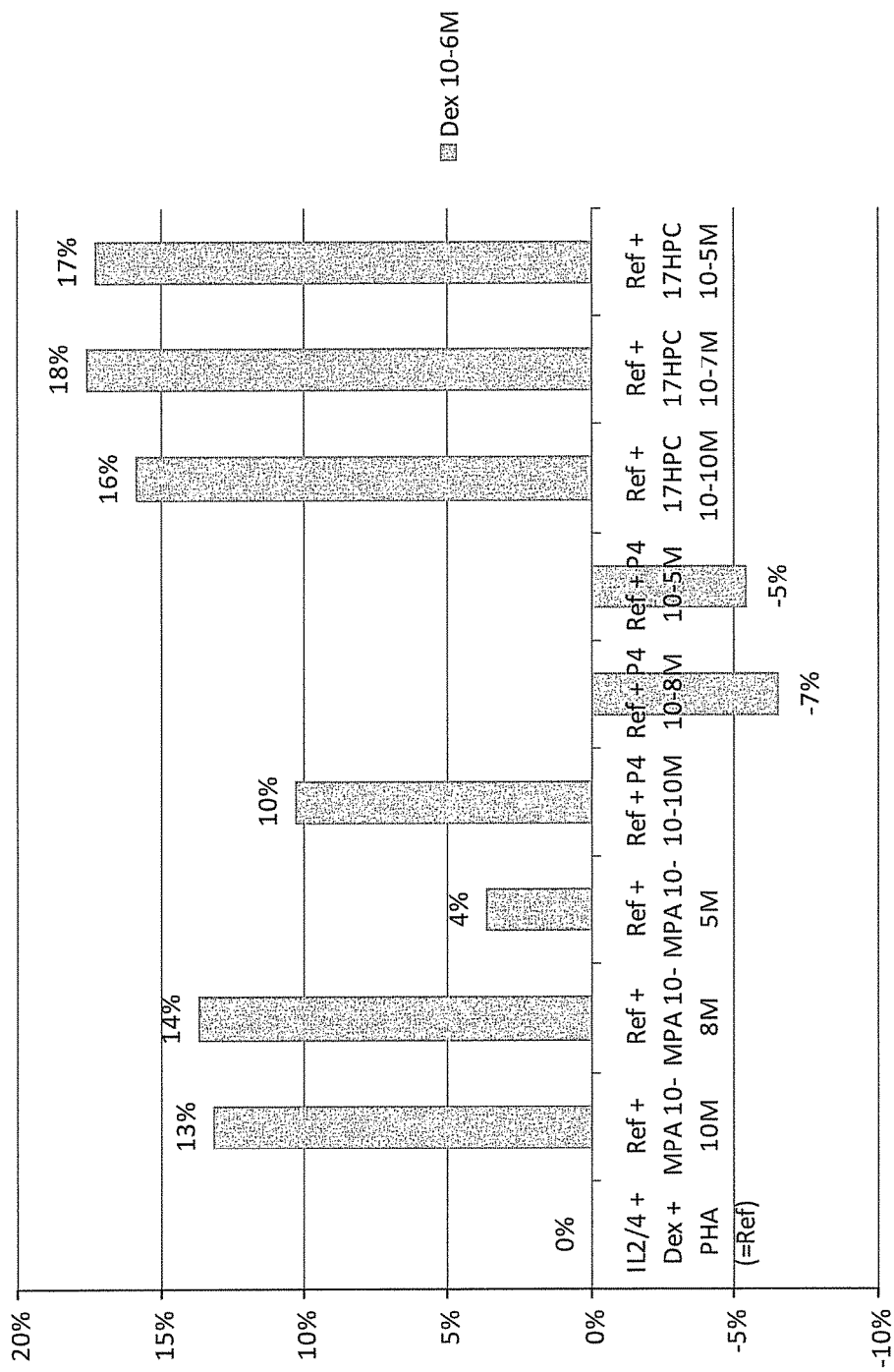

The results depicted in FIGS. 3-4 show that progestogen consistently improves corticosteroid insensitivity by all three progestogen agents (17HPC, P4 and MPA) when the low dose of dexamethasone is used. The Imax improves from 9% to 33%. FIG. 3 depicts progestogen's effects (% Imax) in reversing steroid resistance: comparing 17HPC, P4 and MPA under low dose Dexamethasone ($10^{-10}$ M). FIG. 4 depicts progestogen's effects (% Imax) in reversing steroid resistance: comparing 17HPC, P4 and MPA under high dose dexamethasone ($10^{-6}$ M).

The effects in reversing corticosteroid resistance are observed when the high dose of Dexamethasone is used (FIG. 4). Each progestogen agent has its own dose-response pattern. Among the three tested drugs, 17HPC has the best treatment effects, i.e., highest improvement rate (of 18%) and consistency at all dose levels (16-18%).

Progestogen (e.g., 17HPC, P4 and MPA) thus has the surprising and unexpected effect of reversing glucocorticoid resistance and improving glucocorticoid sensitivity in cigarette smokers. Progestogen, therefore, can be used to treated smoking-induced glucocorticoid resistance diseases such as, for instance, chronic obstructive pulmonary disease (COPD).

Example 3. 17HPC Reverses Corticosteroid Resistance Among Male Smokers

PBMCs ($10^6$ cells/ml) stimulated with IL-2 (13 ng/ml) and IL-4 (6.5 ng/ml) were cultured in 96-well plates for 48 hours and subsequently stimulated with 17HPC ($10^{-10}$ M, $10^{-7}$ M and $10^{-5}$ M) for 12 hours before being exposed with or without three doses of dexamethasone ($10^{-10}$M, $10^{-18}$M and $10^{-6}$ M) for 1 hour, and then were subsequently with PHA (15 µg/mL) for 24 hours at 37° C., 5% CO2 (n=11). IL-2 levels were quantified using ELISA.

Figure 5:
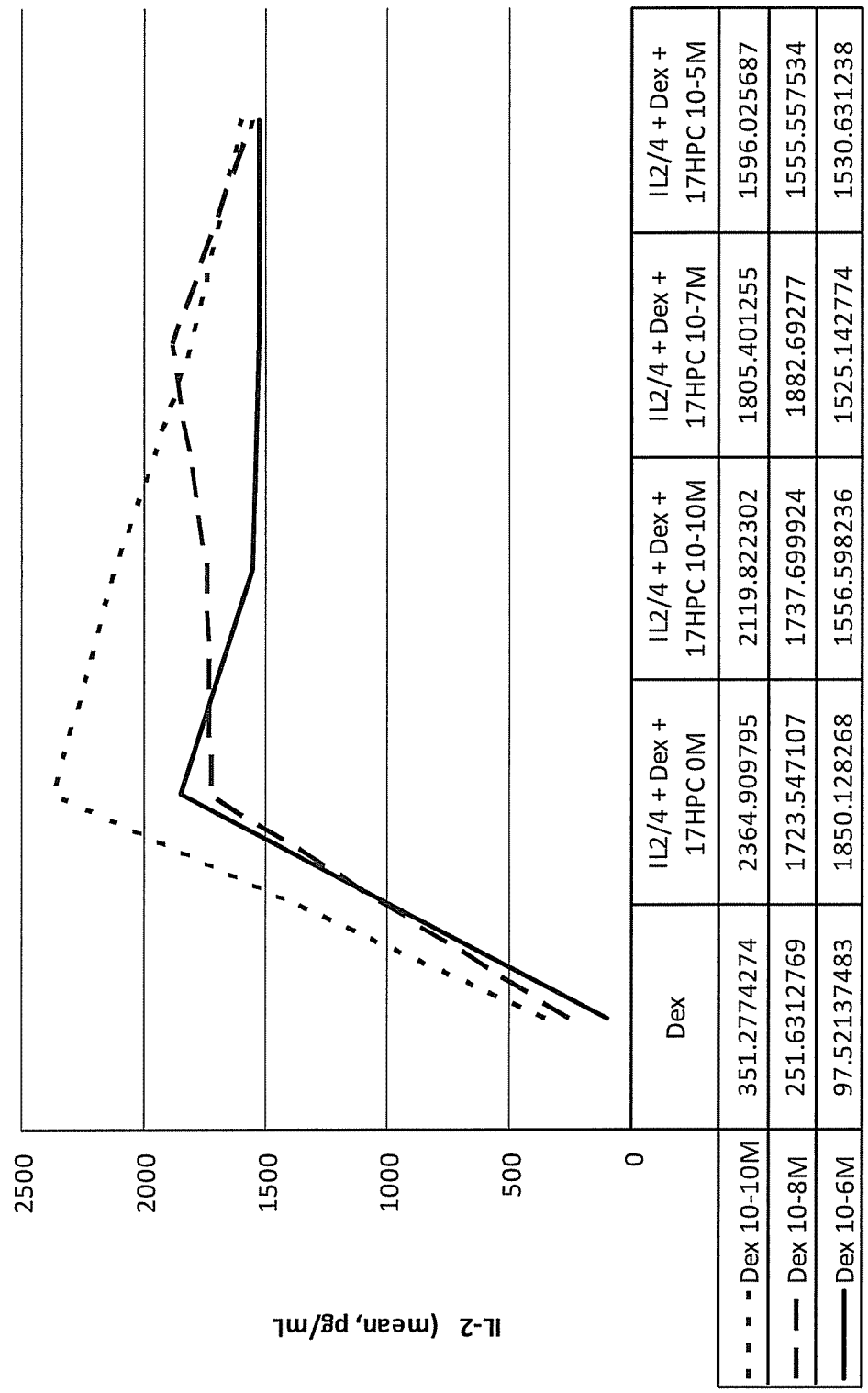

FIG. 5 shows that the addition of IL-2 and IL-4 reduced steroid sensitivity significantly at all three Dexamethasone concentrations. The improvement of dexamethasone inhibition of PHA-induced IL-2 release is achieved by adding 17HPC. 17HPC reverses the glucocorticoid insensitivity in a dose-response pattern. 17HPC thus restores corticosteroid sensitivity. For example, PHA-induced IL-2 level with Dexamethasone$^{-10}$M, but without 17HPC was 2364 pg/mL vs. significantly improved cytokine suppression of 2119, 1805 and 1595 pg/mL after adding 17HPC at $10^{-10}$M, $10^{-7}$M and $10^{-5}$M respectively (p<0.05 in both 17HPC $10^{-7}$M and $10^{-5}$M groups).

FIG. 6 shows individual responses before-and-after 17HPC treatment when the high dose of Dexamethasone $10^{-6}$ M was given. Ten out of 11 subjects had a more than 10% improvement (in % maximal Dexamethasone inhibition) after 17HPC treatment, and only one subject (#6) had no improvement (p<0.05 in Chi Square Test for all three 17HPC dose groups). 17HPC thus reverses steroid resistance and individual response patterns.

Example 4. Individual Response Patterns with Three Progestogen Agents: 17HPC, P4 and MPA Example 3 above showed that Progestogen reverses corticosteroid resistance among male smokers. FIG. 7-9 compares individual response patterns with three progestogen agents: 17HPC, P4 and MPA with the same Dexamethasone dose $10^{-10}$M:

The results depicted in FIG. 7 show that 9 out 11 subjects had a more than 10% improvement in maximal Dexamethasone inhibition after receiving a dose of 17HPC, which is consistent with the results presented in FIG. 6.

The results depicted in FIG. 8 show that 6 out of 8 subjects had a more than 10% improvement in maximal Dexamethasone inhibition after receiving a dose of natural progesterone, which is similar to 17HPC.

The results depicted in FIG. 9 shows that MPA treatment leads a total different response pattern: a "split" response. A sub-group had a great improvement up to 58% while another sub-group presented with a worsening in corticosteroid sensitivity, a reduction up to 88%.

Example 5. Progestogen (e.g., 17HPC) Improves Corticosteroid Sensitivity Under a Non-Steroid Resistant Condition To determine the effect of add-on treatment of 17HPC on glucocorticoid sensitivity simultaneously, PBMCs ($10^6$ cells/ml) were plated in 96-well plates and stimulated with 17HPC ($10^{-11}$ M to $10^{-5}$ M) for 12 hours before being exposed with or without serial dilutions of dexamethasone ($10^{-12}$M to $10^{-6}$ M) for 1 hour, and then were subsequently with PHA (15 µg/mL) for 24 hours at 37° C., 5% CO2. IL-2 levels were quantified using ELISA. $IC_{50}$ values were calculated by using a sigmoidal model (BioDataFit). The value (of IL-2=734) from negative control (i.e., cell+PHA without Dexamethasone or 17HPC) was artificially set as Dexamethasone-$^{18}$M or 17HPC$^{-17}$ M (i.e., assuming drug concentration≈0 M) to fit the sigmoidal model when calculating Dexamethasone-$IC_{50}$ and 17HPC-$IC_{50}$ (N=14).

The effects of 17HPC on dexamethasone sensitivity measured by IL-2 inhibition in smokers are shown in Table 1 and FIG. 10. FIG. 10 shows add-on effect of 17HPC is improvement of steroid sensitivity. 17HPC, especially at lower concentrations, significantly enhances steroid sensitivity measured by Dexamethasone-$IC_{50}$, which is improved from $IC_{50}$=7.5 (Dexamethasone only) to 10.2-12.0 (Dexamethasone+17HPC) (p=0.0052 in ANOVA). The higher dose of 17HPC (at 17HPC $10^{-5}$ M) had minimal or no effect.

TABLE 1

17HPC effect in improving corticosteroid sensitivity (mean IL-2 pg/mL and $IC_{50}$)

| Dexamethasone | Dexamethasone only | 17HPC $10^{-11}$M | 17HPC $10^{-10}$M | 17HPC $10^{-7}$M | 17HPC $10^{-5}$M | PR2005 IC50 |
|---|---|---|---|---|---|---|
| 0 | 734.6692754 | 448.2208447 | 420.6095024 | 466.3103053 | 225.5846837 | 6.434401 |
| $10^{-12}$M | 371.7410856 | 275.1887924 | 132.298398 | 111.5503515 | 176.2274866 | 10.92452 |
| $10^{-10}$M | 312.6599339 | 164.3874069 | 177.7437283 | 104.5164134 | 138.578293 | 11.64492 |
| $10^{-8}$M | 398.132707 | 167.8640405 | 173.5466553 | 229.3011166 | 136.1965467 | 6.242864 |
| $10^{-6}$M | 160.6293856 | 9.050299835 | 27.18227874 | 9.914185277 | 24.6061311 | N/A |
| Dexamethasone IC50 | 7.509749 | 12.01514 | 10.20306 | N/A | 7.595664 | |

Example 6. Progestogen (e.g., 17HPC) has Significant Steroid-Sparing Effects

To determine effect of add-on treatment of 17HPC on glucocorticoid sparing simultaneously, PBMCs ($10^6$ cells/ml) were plated in 96-well plates and stimulated with 17HPC ($10^{-11}$ M to $10^{-5}$ M) for 12 hours before being exposed with or without serial dilutions of dexamethasone ($10^{-12}$M to $10^{-6}$ M) for 1 hour, and then were subsequently with PHA (15 µg/mL) for 24 hours at 37° C., 5% CO2. IL-2 levels were quantified using ELISA. The % inhibition of PHA stimulation of IL-2 (pg/mL) by 17HPC and/or Dexamethasone (Dexamethasone) in PBMCs was calculated. The value (of IL-2=734.7) from the negative control (i.e., cell+PHA without any drug treatment) was set as zero % inhibition, and all other % inhibition values were derived from the formula: (1−(treatment IL-2 level/714.5)×100%, (N=14) (note: 714.5 ng/mL (PHA-induced IL-2) was the mean value from the 14 subjects).

The add-on of 17HPC can achieve similar efficacy by using a lower dose of corticosteroid (Table 2). The percentage of suppression of IL-2 releases by higher dose of $10^{-6}$ M dexamethasone (Imax) in healthy smokers is 78%. The 'add-on' treatment of 17HPC will significantly reduce the dose requirement for Dexamethasone. Table 2 shows that add-on of the low doses of 17HPC ($10^{-11}$ M or $10^{-10}$ M) will achieve a similar anti-inflammatory effect (≥78% IL-2 inhibition) when comparing to Dexamethasone $10^{-6}$ M), i.e., only using the $1/1,000^{th}$ to $1/100,000$th of the original Dexamethasone dose, a substantial steroid-sparing effect. Therefore, the add-on of 17HPC may prevent individuals at risk for developing refractory responses or resistance or exacerbations or tolerance to corticosteroids as well as improving safety profiles.

TABLE 2

Add-on Effect of 17HPC: Steroid-sparing effects measured by % inhibition of PHA stimulation of IL-2

| | Dexamethasone only | 17HPC $10^{-11}$ M | 17HPC $10^{-10}$ M | 17HPC $10^{-7}$ M | 17HPC $10^{-5}$ M |
|---|---|---|---|---|---|
| Dexamethasone 0 M | 0% | 39% | 43% | 37% | 69% |
| Dexamethasone $10^{-12}$ M | 49% | 63% | 82% | 85% | 76% |
| Dexamethasone $10^{-10}$ M | 57% | 78% | 76% | 86% | 81% |
| Dexamethasone $10^{-8}$ M | 46% | 77% | 76% | 69% | 81% |
| Dexamethasone $10^{-6}$ M | 78% | 99% | 96% | 99% | 97% |

Values represent the % inhibition of PHA stimulation of IL-2 (pg/mL) by 17HPC only, Dexamethasone only and 17HPC plus Dexamethasone at different concentrations in the PBMC model.

Example 7. Add-On of Progestogen (e.g., 17HPC) Leads to a Better Treatment Responsiveness, and the Combination of 17HPC with Dexamethasone Results in Synergetic Effects To determine the effect of add-on treatment of 17HPC on glucocorticoid sparing simultaneously, PBMCs ($10^6$ cells/ml) were plated in 96-well plates and stimulated with 17HPC ($10^{-11}$ M to $10^{-5}$ M) for 12 hours before being exposed with or without serial dilutions of dexamethasone ($10^{-12}$M to $10^{-6}$ M) for 1 hour, and then were subsequently with PHA (15 µg/mL) for 24 hours at 37° C., 5% CO2. IL-2 levels were quantified using ELISA. The % inhibition of PHA stimulation of IL-2 (pg/mL) by 17HPC and/or Dexamethasone (Dexamethasone) in PBMCs was calculated. The value (of IL-2=734.7) from the negative control (i.e., cell+PHA without any drug treatment) was set as zero % inhibition, and all other % inhibition values were derived from the formula: (1−(treatment IL-2 level/714.5)×100%, (N=14).

The maximal anti-inflammatory effect of Dexamethasone is 78% inhibition of PHA-induced IL-2 production at $10^{-6}$ M. The 'add-on' treatment of 17HPC produces a significantly better responsiveness and results in near 100% suppression of PHA induced IL-2 (FIG. 11). FIG. 11 thus depicts a better treatment responsiveness with the 17HPC add-on.

Further, the combination of 17HPC with Dexamethasone consistently increases Dexamethasone's anti-inflammatory effects, and is better than their uses individually. FIG. 12 shows that the combination leads to a synergetic effect, with 25-37% improvements in Dexamethasone efficacy. FIG. 12 thus depicts synergetic effects of combination of 17HPC with Dexamethasone.

Example 8. Add-On of Other Progestogen Compounds (e.g., P4 and MPA) Shows Similar Effects in Enhancing Glucocorticoid Sensitivity To determine effect of add-on treatment of MEDROXY-PROGESTERONE ACETATE (MPA) and natural Progesterone (P4) on glucocorticoid sparing simultaneously, PBMCs ($10^6$ cells/ml) were plated in 96-well plates and stimulated with P4 or MPA ($10^{-10}$ M, $10^{-8}$ M and $10^{-5}$ M) for 12 hours before being exposed with or without dexamethasone ($10^{-11}$M to $10^{-8}$ M) for 1 hour, and then were subsequently with PHA (15 µg/mL) for 24 hours at 37° C., 5% CO2 (n=6 for the combinations of P4 or MAP+Dexamethasone). IL-2 levels were quantified using ELISA. The % inhibition of PHA stimulation of IL-2 (pg/mL) by P4, or MPA, and/or Dexamethasone (Dexamethasone) in PBMCs was calculated. The value (of IL-2=765) from the negative control (i.e., cell+PHA without any drug treatment, n=25) was set as zero % inhibition, and all other % inhibition values were derived from the formula: (1−(treatment IL-2 level/765)×100%.

Table 3 and Table 4 show that both P4 and MPA have similar effects in enhancing glucocorticoid sensitivity such as steroid-sparing and synergetic effects of combination. For examples, the percentage of suppression of IL-2 releases by $10^{-8}$ M dexamethasone is improved from 67% to 96% when MPA $10^{-8}$M is added (P=0.035 in pared T-Test). The add-on of the low dose of either P4 or MPA ($10^{-10}$ M) will achieve a similar anti-inflammatory effect (≥86% IL-2 inhibition) when comparing to Dexamethasone $10^{-6}$ M), i.e., only using the $\frac{1}{100}^{th}$ of the original Dexamethasone dose, a substantial steroid-sparing effect.

TABLE 3

Add-on effects of Medroxyprogesterone Acetate (MPA) on enhancing glucocorticoid sensitivity (Mean IL-2 pg/mL and % inhibition of PHA-induced IL-2 production)

|  | MPA $10^{-10}$M | MPA $10^{-8}$M | MPA $10^{-5}$M |
|---|---|---|---|
| PHA | 765.0 (0.0%) | 206.1 (73%) | 166.9 (78%) | 39.8 (95%) |
| DEXAMETHASONE 10E-11M | 216.1 (72%) |  | 129.1 (83%) |  |
| DEXAMETHASONE 10E-8M | 251.6 (67%) | 44.7 (94%) | 29.2 (96%) | 12.3 (98%) |
| DEXAMETHASONE 10E-6M | 109.6 (86%) |  |  |  |

TABLE 4

Add-on effects of natural progesterone (P4) on enhancing glucocorticoid sensitivity (Mean IL-2 pg/mL and % inhibition of PHA-induced IL-2 production)

|  | P4 $10^{-10}$M | P4 $10^{-8}$M | P4 $10^{-5}$M |
|---|---|---|---|
| PHA | 765.0 (0.0%) | 506.9 (34%) | 486.2 (36%) | 113.8 (85%) |
| DEXAMETHASONE 10E-11M | 216.1 (72%) |  | 100.8 (87%) |  |
| DEXAMETHASONE 10E-8M | 251.6 (67%) | 59.6 (92%) | 91.4 (88%) | 81.2 (89%) |
| DEXAMETHASONE 10E-6M | 109.6 (86%) |  |  |  |

What is claimed is:

1. A method for the treatment of either an asthma with glucocorticoid insensitivity condition or a chronic obstructive pulmonary disorder with glucocorticoid insensitivity condition in a patient, said method comprising a step of administering to said patient a pharmaceutical composition comprising 17 alpha-hydroxyprogesterone caproate in an amount effective in alleviating said glucocorticoid insensitivity condition and a pharmaceutically acceptable carrier; wherein the patient has no history of menstrual cycle-related exacerbation;
wherein the effective amount of the pharmaceutical composition is from about 0.001 to about 100 mg/kg of body weight of 17 alpha-hydroxyprogesterone caproate given orally per day.

2. The method of claim 1, wherein the effects of the administration of the pharmaceutical composition comprise steroid-sparing in a corticosteroid-dependent patient, responding to or tolerating of corticosteroids, achieving efficacy by using a low dose of corticosteroid, preventing a patient from developing uncontrollable conditions or resistance or exacerbations in response to antigen exposures, infections, exercise, or irritants, achieving optimal immune-functions, easy administration of steroids that can be tapered or withdrawn, reducing intolerance to prolonged administration of corticosteroids, decreasing risks for developing a corticosteroid-related adverse event, wherein the corticosteroid-related adverse event comprises opportunistic infections or bone loss, or combinations thereof.

3. The method of claim 1, wherein the pharmaceutical composition is administered daily.

4. The method of claim 1, wherein the pharmaceutical composition is administered according to a dosing regimen selected from the group consisting of an administration interval less than one week, once weekly or exceeding once per week.

5. The method of claim 4, wherein the administration interval is selected from the group consisting of once per day, twice per day, three times per day, and up to 24 times per day.

6. The method of claim 4, wherein the administration interval is selected from the group consisting of once every other week, once monthly, once every two months, and once every three months.

7. The method of claim 1, wherein the pharmaceutical composition is administered once monthly.

8. The method of claim 1, wherein the pharmaceutical composition is administered by a formulation selected from the group consisting of solution, emulsion, elixir, tincture, paste, aerosol, capsule, tablet, powder, and a sustained release formulation.

9. The method of claim 1, wherein the 17 alpha-hydroxyprogesterone caproate is administered prior to, simultaneously with, or following glucocorticoid therapy.

10. The method of claim 9, wherein the glucocorticoid is selected from the group consisting of hydrocortisone, cortisone acetate, dexamethasone, prednisone, prednisolone, methylprednisolone, betamethasone, triamcinolone, beclometasone, Paramethasone, fluticasone, fludrocortisone acetate, deoxycorticosterone acetate, Fluprednisolone, fluticasone propionate, budesonide, beclomethasone dipropionate, flunisolide, and triamcinolone acetonide.

11. The method of claim 1, further comprising administering to the patient one or more additional treatments for restoring corticosteroid sensitivity or reversing the glucocorticoid insensitivity or enhancing glucocorticoid sensitivity to treat the asthma with glucocorticoid insensitivity condition or the chronic obstructive pulmonary disorder with glucocorticoid insensitivity condition.

12. The method of claim 11, wherein the one or more additional treatments are administering agents selected from the group consisting of an androgen, an estrogen, an immunosuppressive or immunomodulator agent, a calcineurin inhibitor, a p38 MAP kinase inhibitor, a JNK inhibitor, a vitamin D, an MIF inhibitor, a histone deacetylate-2 activator, a theophylline, a phosphoinositide-3-kinase-δ inhibitor, an antioxidant, an iNOS inhibitor, a p-glycoprotein inhibitor, and combinations thereof.

13. The method of claim 11, wherein the 17 alpha-hydroxyprogesterone caproate is administered prior to, simultaneously with, or following the administration of the one or more additional treatments which are selected from the group consisting of dehydroepiandrosterone, estradiol, cyclosporine, methotrexate, gold, 6-mercaptopurine, infliximab, etanercept, adalimumab, intravenous immunoglobulin, Mepolizumab, cyclosporin, tacrolimus, a p38 MAP kinase inhibitor, a JNK inhibitor, a vitamin D, an MIF inhibitor, a histone deacetylate-2 activator, a theophylline, a phosphoinositide-3-kinase-δ inhibitor, an antioxidant, an iNOS inhibitor, a p-glycoprotein inhibitor, and combinations thereof.

14. A method of treating a smoking-induced glucocorticoid insensitivity condition in a patient, said method comprising a step of administering to said patient a pharmaceutical composition comprising 17 alpha-hydroxyprogesterone caproate in an amount effective in alleviating said glucocorticoid insensitivity condition and a pharmaceutically acceptable carrier;

wherein the patient has no history of menstrual cycle-related exacerbation;

wherein the effective amount of the pharmaceutical composition is from about 0.001 to about 100 mg/kg of body weight of 17 alpha-hydroxyprogesterone caproate given orally per day.

15. A method of treating a glucocorticoid insensitivity condition in a patient with an increased IL-2 production, said method comprising a step of administering to said patient a pharmaceutical composition comprising 17 alpha-hydroxyprogesterone caproate in an amount effective in reducing interleukin-2 levels and a pharmaceutically acceptable carrier;

wherein the effective amount of the pharmaceutical composition is from about 0.001 to about 100 mg/kg of body weight of 17 alpha-hydroxyprogesterone caproate given orally per day.

16. The method of 1, wherein the effective amount is selected such that the glucocorticoid insensitivity condition is improved by more than 10%.

* * * * *